United States Patent [19]

Chakravarty et al.

[11] Patent Number: 5,223,501
[45] Date of Patent: * Jun. 29, 1993

[54] SUBSTITUTED PYRIMIDINONES BEARING ACIDIC FUNCTIONAL GROUPS AS ANGIOTENSIN II ANTAGONISTS

[75] Inventors: Prasun K. Chakravarty, Edison; Nathan B. Mantlo, Westfield; William J. Greenlee, Teaneck; Arthur A. Patchett, Westfield; Dooseop Kim, Scotch Plains, all of N.J.

[73] Assignee: Merck & Co., Inc., Rahway, N.J.

[*] Notice: The portion of the term of this patent subsequent to Apr. 13, 2010 has been disclaimed.

[21] Appl. No.: 698,440

[22] Filed: May 10, 1991

[51] Int. Cl.$^5$ .............. A61K 31/505; C07D 487/00; C07D 473/00
[52] U.S. Cl. .................. 514/258; 514/262; 544/244; 544/255; 544/262; 544/278; 544/280; 544/284; 544/289; 544/2; 544/97
[58] Field of Search ............... 544/244, 262, 280, 284, 544/289, 255, 278, 2, 97; 514/258, 262

[56] References Cited

U.S. PATENT DOCUMENTS

| | | | |
|---|---|---|---|
| 4,804,658 | 2/1989 | Manley et al. | 544/127 |
| 4,880,804 | 11/1989 | Carini et al. | 544/139 |

FOREIGN PATENT DOCUMENTS

| | | |
|---|---|---|
| 2020370 | 1/1991 | Canada . |
| 0253310 | 1/1988 | European Pat. Off. . |
| 0407342A3 | 1/1991 | European Pat. Off. . |
| 0443568A1 | 8/1991 | European Pat. Off. . |
| 0481614A1 | 4/1992 | European Pat. Off. . |

OTHER PUBLICATIONS

Piper et al. J. Med. Chem. vol. 23, pp. 1136-1139 1980.
P. C. Wong, et al., European J. Pharma., 202, p. 323 (1991).

Primary Examiner—John M. Ford
Assistant Examiner—Y. N. Gupta
Attorney, Agent, or Firm—Joseph F. DiPrima; William H. Nicholson; Valerie J. Camara

[57] ABSTRACT

Novel substituted fused pyrimidinones of formula (I) are useful as angiotensin II antagonists.

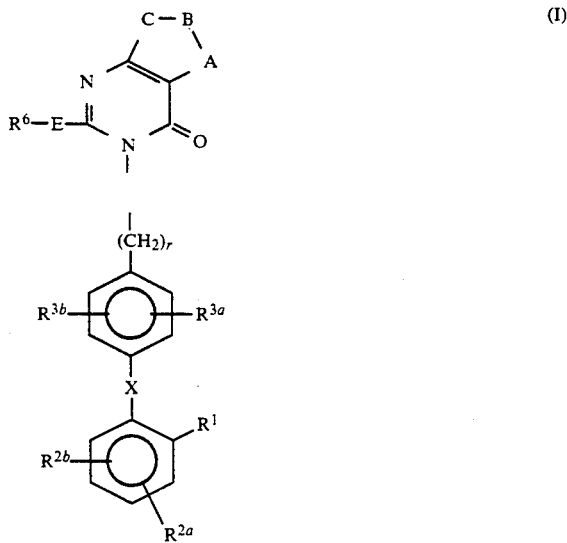

6 Claims, No Drawings

SUBSTITUTED PYRIMIDINONES BEARING ACIDIC FUNCTIONAL GROUPS AS ANGIOTENSIN II ANTAGONISTS

INTRODUCTION OF THE INVENTION

This invention relates to novel substituted fused pyrimidinone compounds which are useful as angiotensin II antagonists in the treatment of elevated blood pressure and congestive heart failure.

The compounds of this invention also have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

BACKGROUND OF THE INVENTION

The renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by their partial agonist activity and lack of oral absorption [M. Antonaccio. *Clin. Exp. Hypertens.* A4, 27-46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246-271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; 291,969; 323,841; 324,377; 403,158; 403,159; 407,342; 411,507; 412,848; and 415,886; and in articles by A. T. Chiu, et al. [*Eur. J. Pharm. Exp. Therap*, 157, 13-21 (1988)] and by P. C. Wong, et al. [*J. Pharm. Exp. Therap*, 247, 1-7(1988), *Hypertension*, 13, 489-497 (1989)]. European Patent Applications 028,834 and 253,310 and the above three articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

DETAILED DESCRIPTION OF THE INVENTION

This invention relates to novel substituted fused pyrimidinone compounds which are useful as angiotensin II antagonists, primarily as antihypertensives. The compounds of this invention have the general formula (I):

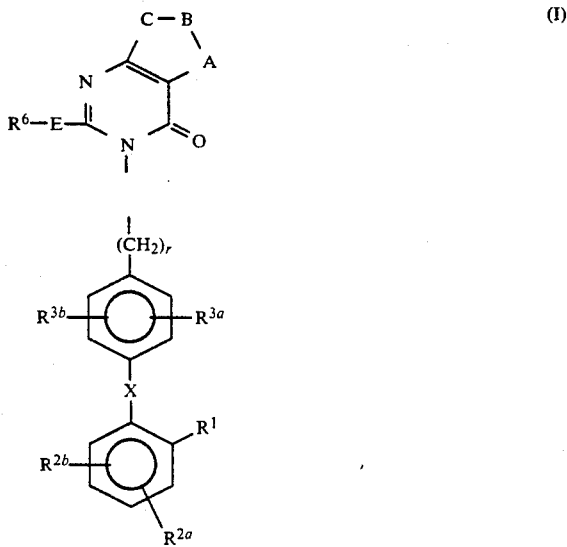

wherein:

A—B—C together with the pyrimidinone to which it is attached form a member selected from the group:

(a) 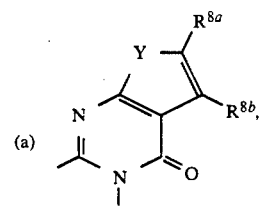

(b) 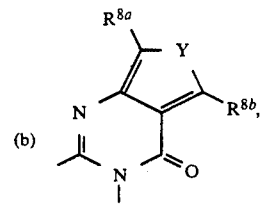

(c) 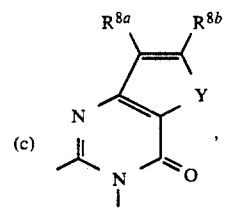

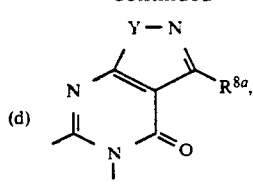
(d)
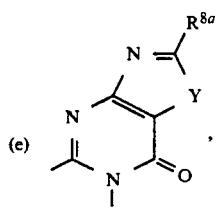
(e)
$R^1$ is
(a) $-SO_2N(R^{24})-OR^{24}$,
(b) $-SO_2NHSO_2R^{23}$,
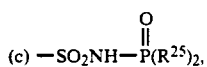
(c)
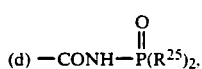
(d)
(e) $-SO_2NHCN$,
(f) $-SO_2NHCO_2R^{23}$,
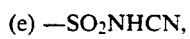
(g)
(h) $-NHSO_2NHSO_2R^{23}$,
(i)
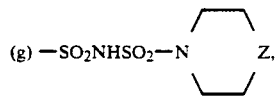
(f)
(g)
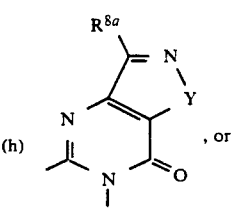
(h)
(i)
Y is O, S or $NR^7$;
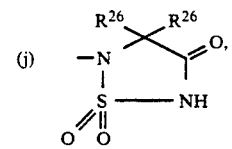
(j)
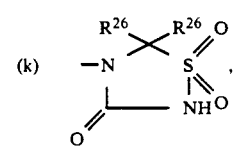
(k)
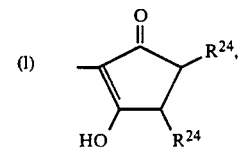
(l)
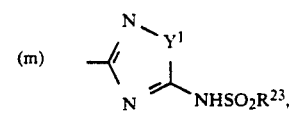
(m)
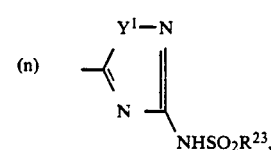
(n)
(o) $-SO_2NHSO_2-N\begin{matrix}R^4\\R^9\end{matrix}$,
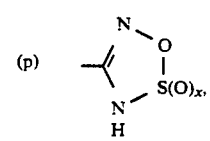
(p)

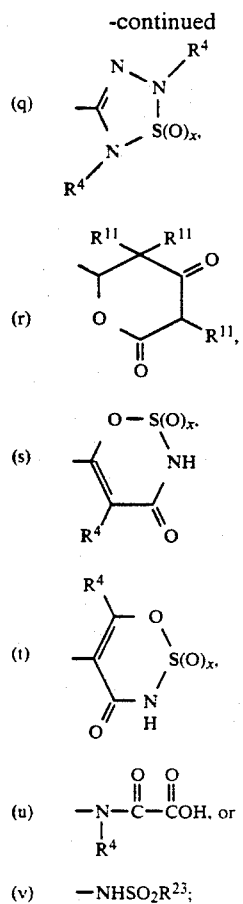

wherein $Y^1$ is O or S;
$R^{2a}$ and $R^{2b}$ are each independently
  (a) H,
  (b) Cl, Br, I, or F,
  (c) $NO_2$,
  (d) $NH_2$,
  (e) $C_1$-$C_4$-alkylamino,
  (f) di($C_1$-$C_4$-alkyl)amino,
  (g) $SO_2NHR^9$,
  (h) $CF_3$,
  (i) $C_1$-$C_6$-alkyl,
  (j) $C_1$-$C_6$-alkoxy,
  (k) $C_1$-$C_6$-alkyl-S-,
  (l) $C_2$-$C_6$-alkenyl,
  (m) $C_2$-$C_6$-alkynyl,
  (n) aryl,
  (o) aryl($C_1$-$C_4$-alkyl), or
  (p) $C_3$-$C_7$-cycloalkyl;
$R^{3a}$ is
  (a) H,
  (b) Cl, Br, I, or F,
  (c) $C_1$-$C_6$-alkyl,
  (d) $C_1$-$C_6$-alkoxy, or
  (e) $C_1$-$C_6$-alkoxyalkyl;
$R^{3b}$ is
  (a) H
  (b) Cl, Br, I, or F,
  (c) $NO_2$,
  (d) $C_1$-$C_6$-alkyl,
  (e) $C_1$-$C_6$-acyloxy,
  (f) $C_3$-$C_7$-cycloalkyl,
  (g) $C_1$-$C_6$-alkoxy, (h) $-NHSO_2R^4$,
  (i) hydroxy($C_1$-$C_4$-alkyl),
  (j) aryl($C_1$-$C_4$-alkyl),
  (k) $C_1$-$C_4$-alkylthio,
  (l) $C_1$-$C_4$-alkyl sulfinyl,
  (m) $C_1$-$C_4$-alkyl sulfonyl,
  (n) $NH_2$,
  (o) $C_1$-$C_4$-alkylamino,
  (p) di($C_1$-$C_4$-alkyl)amino,
  (q) fluoro-$C_1$-$C_4$-alkyl-,
  (r) $-SO_2-NHR^9$,
  (s) aryl,
  (t) furyl,
  (u) $CF_3$,
  (v) $C_2$-$C_6$-alkenyl, or
  (w) $C_2$-$C_6$-alkynyl;
wherein aryl is phenyl or naphthyl or substituted phenyl or naphthyl with one or two substituents selected from the group consisting of Cl, Br, I, F, $N(R^4)_2$, $CO_2R^4$, $C_1$-$C_4$-alkyl, $C_1$-$C_4$-alkoxy, $NO_2$, $CF_3$, $C_1$-$C_4$-alkylthio, OH, $-SO_2NR^9R^{10}$, $C_3$-$C_7$-cycloalkyl, $C_3$-$C_{10}$-alkenyl, and $-SO(C_1$-$C_4$-alkyl);
$R^4$ is H, aryl as defined hereinabove, $C_1$-$C_6$ alkyl, or substituted $C_1$-$C_6$ alkyl with an aryl or heteroaryl substituent, wherein the heteroaryl is an unsubstituted, monosubstituted or disubstituted heteroaromatic 5 or 6 membered ring which contains one to three heteroatoms selected from the group consisting of N, O and S, and wherein the substituents are members selected from the group consisting of —OH, —SH, $C_1$-$C_4$-alkyl, $C_1$-$C_4$-alkoxy, $-CF_3$, Cl, Br, I, F, and $NO_2$;
$R^{4a}$ is aryl, $C_1$-$C_6$ alkyl, or aryl-$C_1$-$C_6$-alkyl;
$R^5$ is

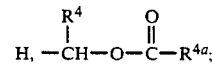

E is a single bond, $-NR^{13}(CH_2)_s-$, $-S(O)_x(CH_2)_s-$ where x is 0 to 2 and s is 0 to 5, $-CH(OH)-$, $-O-$, CO—;
$R^6$ is
  (a) aryl,
  (b) $C_1$-$C_6$-alkyl, $C_2$-$C_5$-alkenyl or $C_2$-$C_5$-alkynyl or substituted $C_1$-$C_6$-alkyl, $C_2$-$C_5$-alkenyl or $C_2$-$C_5$-alkynyl substituted with a substituent selected from the group consisting of aryl, $C_3$-$C_7$-cycloalkyl, Cl, Br, I, F, $CF_3$, $CF_2CF_3$, $-NH_2$, $-NH(C_1$-$C_4$-alkyl), $-OR^4$ $-N(C_1$-$C_4$-alkyl)$_2$, $-NH-SO_2R^4$, $-COOR^4$, $-SO_2NHR^9$,
  (c) heteroaryl as defined hereinabove;
  (d) $C_3$-$C_7$-cycloalkyl,
  (e) perfluoro-$C_1$-$C_4$-alkyl, or
  (f) H;
$R^7$ is:
  (a) H,
  (b) $C_1$-$C_6$-alkyl, $C_2$-$C_6$-alkenyl or $C_2$-$C_6$-alkynyl or substituted $C_1$-$C_6$-alkyl, $C_2$-$C_6$-alkenyl or $C_2$-$C_6$-alkynyl substituted with a substituent selected from the group consisting of $C_3$-$C_7$-cycloalkyl, Cl, Br, I, F, —OH, $-NH_2$, $-NH(C_1$-$C_4$-alkyl), $-N(C_1$-$C_4$ alkyl)$_2$, $-NHSO_2R^4$, $-COOR^4$, $C_1$-$C_4$-alkoxyl, $C_1$-$C_4$-alkylthio, $-CONH_2$, $-COR^4$, $-SO_2R^4$, $-NR^4COR^{22}$, $-NR^4CO_2R^{22}$, $-NR^4CONR^4R^{22}$ or —CO heteroaryl,
  (c) $-COR^4$, (d) phenyl or naphthyl or substituted phenyl or naphthyl with one or two substituents selected from the group consisting of V or W,
(e) phenyl-$C_1$-$C_6$-alkyl or naphthyl-$C_1$-$C_6$-alkyl in which the phenyl or naphthyl group is unsubstituted, mono- or disubstituted with V or W,
(f) —$OR^4$,
(g) heteroaryl, or
(h) —$CON(R^4)_2$;

V and W are independently:
(a) H,
(b) $C_1$-$C_5$-alkoxy,
(c) $C_1$-$C_5$-alkyl,
(d) hydroxy,
(e) $C_1$-$C_5$-alkyl-$S(O)_x$-,
(f) CN,
(g) $NO_2$,
(h) $N(R^4)_2$,
(i) $CON(R^4)_2$,
(j) $CO_2R^4$,
(k) $COR^4$,
(l) $CF_3$,
(m) Cl, Br, I, or F,
(n) hydroxy-$C_1$-$C_5$-alkyl,
(o) $C_1$-$C_5$-alkylthio,
(p) —$SO_2NR^9R^{10}$,
(q) $C_3$-$C_7$-cycloalkyl, or
(r) $C_2$-$C_{10}$-alkenyl;

$R^{8a}$ and $R^{8b}$ are independently
(a) H,
(b) $C_1$-$C_8$-alkyl, $C_2$-$C_6$-alkenyl or $C_2$-$C_6$-alkynyl or substituted $C_1$-$C_8$-alkyl, $C_2$-$C_6$-alkenyl or $C_2$-$C_6$-alkynyl with a substituent selected from the group consisting of —OH, -guanidino, $C_1$-$C_4$-alkoxy, —$N(R^4)_2$, $COOR^4$, —$CON(R^4)_2$, —O—$COR^4$, -aryl, -heteroaryl, —$S(O)_x$—$R^{22}$, -tetrazol-5-yl, —$CONHSO_2R^{22}$, —$SO_2NH$-heteroaryl, —$SO_2NHCOR^{22}$, —$PO(OR^4)_2$, —$PO(OR^4)R^9$, —$SO_2NH$-CN, —$NR^{10}COOR^{22}$, —$(CH_2)_{1-4}R^4$, Cl, Br, F, or I,
(c) —CO-aryl,
(d) —$C_3$-$C_7$-cycloalkyl,
(e) Cl, Br, I, or F,
(f) —OH,
(g) —$OR^{22}$,
(h) —$C_1$-$C_4$-perfluoroalkyl,
(i) —$S(O)_x$—$R^{22}$,
(j) —$COOR^4$,
(k) —$SO_3H$,
(l) —$NR^{22a}R^{22}$,
(m) —$NR^{22a}COR^{22}$,
(n) —$NR^{22a}COOR^{22}$,
(o) —$SO_2NR^4R^9$,
(p) —$NO_2$,
(q) —$N(R^{22a})SO_2R^{22}$,
(r) —$NR^{22a}CONR^4R^{22}$,

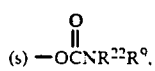

(t) -aryl or -heteroaryl,
(u) —$SO_2NH$-heteroaryl,
(v) —$SO_2NHCOR^{22}$,
(w) —$CONHSO_2R^{22}$,
(x) —$PO(OR^4)_2$,
(y) —$PO(OR^4)R^4$,
(z) -tetrazol-5-yl, (aa) —$CONH$(tetrazol-5-yl),
(bb) —$COR^4$,
(cc) —$SO_2NHCN$,
(dd) —$NR^4SO_2NR^4R^{22}$,
(ee) —$NR^4SO_2OR^{22}$,
(ff) —$CONR^4R^{22}$,

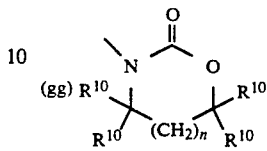

where n = 0 or 1, or

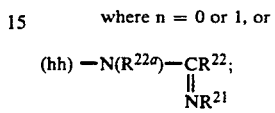

$R^9$ is H, $C_1$-$C_5$-alkyl, aryl or arylmethyl;
$R^{10}$ is H, $C_1$-$C_4$-alkyl;
$R^{11}$ is H, $C_1$-$C_6$-alkyl, $C_1$-$C_4$-alkenyl, $C_1$-$C_4$-alkoxy alkyl, or

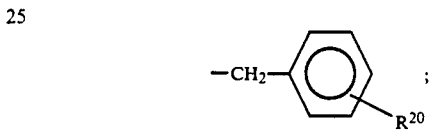

$R^{12}$ is —CN, —$NO_2$, —$CF_3$ or —$CO_2R^4$;
$R^{13}$ is H, ($C_1$-$C_4$-alkyl)CO—, $C_1$-$C_6$-alkyl, allyl, $C_3$-$C_6$-cycloalkyl, aryl or arylmethyl;
$R^{14}$ is H, $C_1$-$C_8$-alkyl, $C_1$-$C_8$-perfluoroalkyl, $C_3$-$C_6$-cycloalkyl, aryl or arylmethyl;
$R^{15}$ is H, $C_1$-$C_6$-alkyl;
$R^{16}$ is H, $C_1$-$C_6$-alkyl, $C_3$-$C_6$-cycloalkyl, aryl or arylmethyl;
$R^{17}$ is —$NR^9R^{10}$, —$OR^{10}$, —$NHCONH_2$, —$NHCSNH_2$,

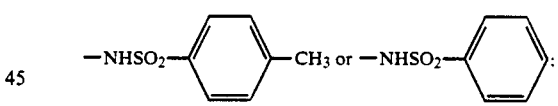

$R^{18}$ and $R^{19}$ are independently $C_1$-$C_4$-alkyl or taken together are —$(CH_2)_q$— where q is 2 or 3;
$R^{20}$ is H, —$NO_2$, —$NH_2$, —OH or —$OCH_3$;
$R^{21}$ is
(a) aryl,
(b) heteroaryl, or
(c) $C_1$-$C_4$-alkyl or substituted $C_1$-$C_4$-alkyl with a substituent selected from the group consisting of aryl, heteroaryl, —OH, —$NH_2$, —$NH(C_1$-$C_4$-alkyl), —$N(C_1$-$C_4$-alkyl)$_2$, —$CO_2R^{4a}$, Cl, Br, F, I, or —$CF_3$;
$R^{22}$ is
(a) aryl,
(b) heteroaryl,
(c) $C_3$-$C_7$-cycloalkyl,
(d) $C_1$-$C_6$-alkyl or substituted $C_1$-$C_6$-alkyl with a substituent selected from the group consisting of aryl, heteroaryl, —OH, —SH, $C_1$-$C_4$-alkyl, —O($C_1$-$C_4$-alkyl), —S($C_1$-$C_4$-alkyl), —$CF_3$, Cl, Br, F, I, —$NO_2$, —$CO_2H$, $CO_2$—($C_1$-$C_4$-alkyl), —$NH_2$, —$NH(C_1$-$C_4$-alkyl), —$N(C_1$-$C_4$-alkyl)$_2$, —PO$_3$H$_2$, —PO(OH)(O—C$_1$-C$_4$-alkyl), —PO(OR$^4$)R$^9$, morpholinyl or N—(C$_1$-C$_4$ alkyl)-piperazinyl, or (e) perfluoro-C$_1$-C$_4$-alkyl;

R$^{22a}$ is
(a) hydrogen,
(b) aryl,
(c) heteroaryl,
(d) C$_3$-C$_7$-cycloalkyl,
(e) C$_1$-C$_6$-alkyl or substituted C$_1$-C$_6$-alkyl with a substituent selected from the group consisting of aryl, heteroaryl, —OH, —SH, C$_1$-C$_4$-alkyl, —O(C$_1$-C$_4$-alkyl), —S(C$_1$-C$_4$-alkyl), —CF$_3$, Cl, Br, F, I, —NO$_2$, —CO$_2$H, CO$_2$—(C$_1$-C$_4$-alkyl), —NH$_2$, —NH(C$_1$-C$_4$-alkyl), —N(C$_1$-C$_4$-alkyl)$_2$, —PO$_3$H$_2$, —PO(OH)(O—C$_1$-C$_4$-alkyl), —PO(OR$^4$)R$^9$, morpholinyl or N—(C$_1$-C$_4$-alkyl)-piperazinyl, or
(f) perfluoro-C$_1$-C$_4$-alkyl;

R$^{23}$ is
(a) aryl,
(b) heteroaryl,
(c) C$_3$-C$_4$-cycloalkyl,
(d) C$_1$-C$_4$-alkyl or substituted C$_1$-C$_4$ alkyl with a substituent that is a member selected from the group consisting of aryl, heteroaryl, —OH, —SH, —C$_1$-C$_4$-alkyl, —C$_3$-C$_7$-cycloalkyl, —O(C$_1$-C$_4$-alkyl), —S(O)$_x$(C$_1$-C$_4$-alkyl), —CF$_3$, Cl, Br, F, I, —NO$_2$, —CO$_2$H, —CO$_2$—C$_1$-C$_4$-alkyl, —NH$_2$, —NH(C$_1$-C$_4$-alkyl), —NHCOR$^{4a}$, —N(C$_1$-C$_4$-alkyl)$_2$, —PO(OH)(C$_1$-C$_4$-alkyl), —PO(OH)(aryl), or —PO(OH)(O—C$_1$-C$_4$-alkyl); where x is 0 to 2, or
(e) perfluoro-C$_1$-C$_4$-alkyl;

R$^{24}$ is
(a) H,
(b) aryl as defined above, or
(c) C$_1$-C$_6$-alkyl optionally substituted with aryl, F, Cl, Br, —OH, —NH$_2$, —NH(C$_1$-C$_4$-alkyl), —N(-C$_1$-C$_4$-alkyl)$_2$, or CF$_3$;

R$^{25}$ is
(a) aryl as defined above,
(b) C$_1$-C$_6$-alkyl optionally substituted with aryl, F, Cl, Br, —OH, —NH$_2$, —NH(C$_1$-C$_4$-alkyl), —N(-C$_1$-C$_4$-alkyl)$_2$, CF$_3$, —COOR$^4$, or CN,
(c) —OCH(R$^4$)—O—CO—R$^{4a}$, or
(d) —OH, —O—C$_1$-C$_6$-alkyl wherein alkyl is as defined in (b);

R$^{26}$ is
(a) H,
(b) C$_1$-C$_6$-alkyl optionally substituted with aryl, F, Cl, Br, —OH, —NH$_2$, —NH(C$_1$-C$_4$-alkyl), —N(-C$_1$-C$_4$-alkyl)$_2$, CF$_3$, —COOR$^4$, or CN, or
(c) F, Cl, Br;

X is
(a) a carbon-carbon single bond,
(b) —CO—,
(c) —O—,
(d) —S—, (e) —N—,
    |
    R$^{13}$ (f) —CON—,
    |
    R$^{15}$ -continued (g) —NCO—,
    |
    R$^{15}$ (h) —OCH$_2$—,
(i) —CH$_2$O—
(j) —SCH$_2$—,
(k) —CH$_2$S—,
(l) —NHC(R$^9$)(R$^{10}$),
(m) —NR$^9$SO$_2$—,
(n) —SO$_2$NR$^9$—,
(o) —C(R$^9$)(R$^{10}$)NH—,
(p) —CH=CH—,
(q) —CF=CF—,
(r) —CH=CF—,
(s) —CF=CH—,
(t) —CH$_2$CH$_2$—,
(u) —CF$_2$CF$_2$—, (v) —HC$\overset{\diagup CH_2 \diagdown}{\text{———}}$CH— or $\overset{\diagup CH_2 \diagdown}{\underset{\diagdown CH_2 \diagup}{C}}$ $\Bigg|$ CH$_2$ (w) —CH—,
     |
     OR$^{14}$ (x) —CH—
     |
     OCOR$^{16}$ (y) —C—, or
     ||
     NR$^{17}$ (z) —C— ;
    $\diagup \diagdown$
  R$^{18}$O  OR$^{19}$ r is 1 or 2; and
the pharmaceutically acceptable salts thereof.

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

One embodiment of the compounds of formula (I) are those compounds wherein:

R$^1$ is:
(a) —SO$_2$N(R$^{24}$)—OR$^{24}$,
(b) —SO$_2$NHSO$_2$R$^{23}$, (c) —SO$_2$NH—$\overset{O}{\underset{||}{P}}$(R$^{25}$)$_2$, (d) —SO$_2$NHCN,
(e) —SO$_2$NHCO$_2$R$^{23}$, (f) —SO$_2$NHSO$_2$—N$\diagup\diagdown$Z,
              $\diagdown\diagup$ (g) —SO$_2$NHSO$_2$—N(R$^4$)(R$^9$), (h) —NHSO$_2$NHSO$_2$R$^{23}$, or (i)  —NHSO$_2$NHP(R$^{25}$)$_2$;

(j) 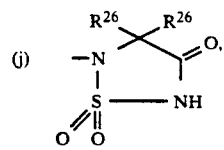

(k) 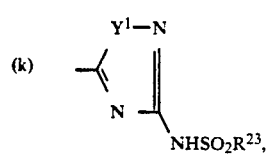

(l) 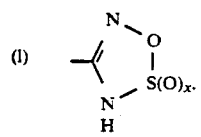

(m) 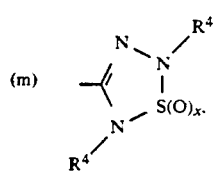

(n) 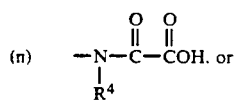

(o) 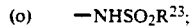 —NHSO$_2$R$^{23}$;

Y$^1$ is O or S;
R$^{2a}$ is H;
R$^{2b}$ is H, F, Cl, CF$_3$, C$_1$-C$_6$-alkyl, C$_2$-C$_6$-alkenyl, C$_2$-C$_6$-alkynyl, or aryl;
R$^{3a}$ is H;
R$^{3b}$ is H, F, Cl, CF$_3$, C$_1$-C$_4$-alkyl, C$_2$-C$_4$-alkenyl, C$_2$-C$_4$-alkynyl, C$_5$-C$_6$-cycloalkyl, —COOCH$_3$, —COOC$_2$H$_5$, —SO$_2$—CH$_3$, NH$_2$, —N(C$_1$-C$_4$-alkyl)$_2$ or —NH—SO$_2$CH$_3$;
E is a single bond, —O— or —S—;
R$^6$ is
  (a) C$_1$-C$_5$ alkyl or substituted C$_1$-C$_5$ alkyl with a substituent selected from the group consisting of C$_3$-C$_5$-cycloalkyl, Cl, CF$_3$, CCl$_3$, —O—CH$_3$, —OC$_2$H$_5$, —S—CH$_3$, —S—C$_2$H$_5$, phenyl, or F,
  (b) C$_2$-C$_5$-alkenyl or C$_2$-C$_5$-alkynyl, or
  (c) C$_3$-C$_5$-cycloalkyl;
R$^7$ is
  (a) H,
  (b) C$_1$-C$_6$-alkyl or substituted C$_1$-C$_6$-alkyl with a —OH, —N(R$^4$)$_2$, —NR$^4$COR$^{22}$ —NR$^4$CO$_2$R$^{22}$, —NR$^4$CONR$^4$R$^{22}$ substituent, or
  (c) phenyl or naphthyl or substituted phenyl or naphthyl with a Cl, —F, —O(C$_1$-C$_4$-alkyl), —CO$_2$R$^4$, —SO$_2$R$^4$ substituent;
R$^{8a}$ and R$^{8b}$ are independently
  (a) H,
  (b) C$_1$-C$_8$-alkyl or substituted C$_1$-C$_8$-alkyl with COOR, OCOR$^{4a}$, OH, aryl, or —(CH$_2$)$_{1-4}$R$^4$ substituent, (c) OR$^{22}$,
(d) —OH,
(e) —NO$_2$,
(f) —N(R$^{22a}$)COR$^{22}$,
(g) —CONR$^4$R$^{22}$,
(h) —N(R$^{22a}$)CO$_2$R$^{22}$,
(i) —NR$^4$R$^{22}$,
(j) Cl, F, or Br,
(k) —CF$_3$,
(l) —CO$_2$R$^{4a}$,
(m) —CO—aryl,
(n) —S(O)$_x$—R$^{22}$,
(o) —SO$_2$—NR$^4$R$^9$,
(p) —N(R$^{22a}$)SO$_2$R$^{22}$,
(q) aryl,
(r) —N(R$^{22a}$)CONR$^4$R$^{22}$, or
(s) —N(R$^{22a}$)SO$_2$N(R$^4$)R$^{22}$;

X is a single bond; and
r is one.

In a class of this embodiment are those compounds of Formula (I) wherein:

A—B—C together with the pyrimidinone to which it is attached form a member selected from the group:

(a) 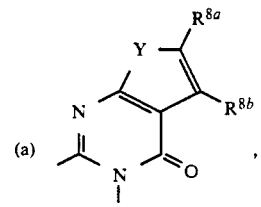, (b) 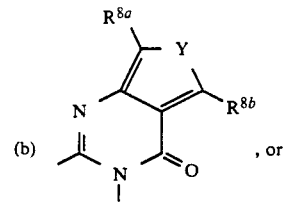, or (c) 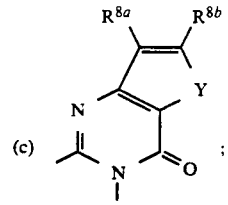;

Y is O, S or NR$^7$;
E is a single bond;
R$^{2b}$ and R$^{3b}$ are H;
R$^6$ is C$_1$-C$_4$-alkyl, C$_2$-C$_5$-alkenyl, cyclopropyl, —CH$_2$CH$_2$CF$_3$, —CH$_2$CH$_2$CH$_2$CF$_3$ or cyclopropylmethyl; and
R$^{8a}$ and R$^{8b}$ are each independently H, —C$_1$-C$_4$ alkyl, —NO$_2$, —NR$^4$R$^{22}$, —OCH$_3$, —NR$^{22a}$COOR$^{22}$, —Cl, CH$_2$COOR$^{4a}$, —S(O)$_x$—R$^{22}$, —NR$^{22a}$CONR$^4$R$^{22}$, —CH$_2$OCO(C$_1$-C$_4$-alkyl), —NR$^{22a}$COR$^{22}$, —CO$_2$R$^{4a}$, —F, —CH$_2$Ph, or —CONR$^4$R$^{22}$.

Exemplifying this subclass are the following compounds of the formula II shown in Table A:

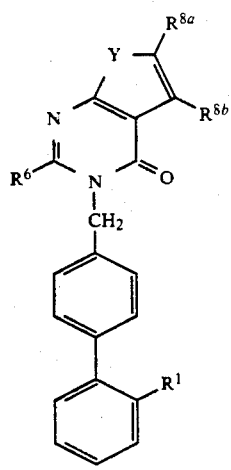

(II)

TABLE A

| Compound No. | R¹ | R⁶ | R⁸ᵇ | R⁸ᵃ | Y |
|---|---|---|---|---|---|
| A1 | —SO₂NHOH | Bu | Me | iPr | S |
| A2 | —SO₂NHSO₂Ph | Bu | Me | iPr | S |
| A3 | —SO₂NHSO₂Me | Pr | Me | Me | O |
| A4 | —SO₂NHSO₂-iPr | Pr | CO₂H | Me | S |
| A5 | (methyl-oxadiazole-sulfonyl, NH) | Bu | Me | Me | S |
| A6 | (methyl-triazole-N-Ph, S=O, NH) | Bu | Me | Me | S |
| A7 | —NH—C(O)—CO₂H | Pr | CO₂H | Me | S |
| A8 | —SO₂NHSO₂-iPr | Pr | Me | Ph | O |
| A9 | —SO₂NHP(O)(O—CH₂Ph)₂ | Bu | Me | Me | S |
| A10 | (cyclic sulfamide with C=O) | Bu | Me | Me | S |
| A11 | (oxadiazole-NHSO₂Ph) | Pr | Me | Me | S |
| A12 | (methyl-oxadiazole-sulfonyl, NH) | Bu | Me | Me | S |
| A13 | —NHSO₂-(thienyl) | Bu | CO₂H | i-Pr | O |
| A14 | —NHSO₂-(2,4-difluorophenyl) | Bu | Me | iPr | S |
| A15 | —SO₂NHCO₂Et | Bu | Me | iPr | S |
| A16 | —SO₂NHCO₂i-Pr | Bu | Me | iPr | S |
| A17 | —SO₂NHPO(OEt)₂ | Bu | Me | iPr | S |

Exemplifying this subclass are the following compounds of the Formula III shown in Table B:

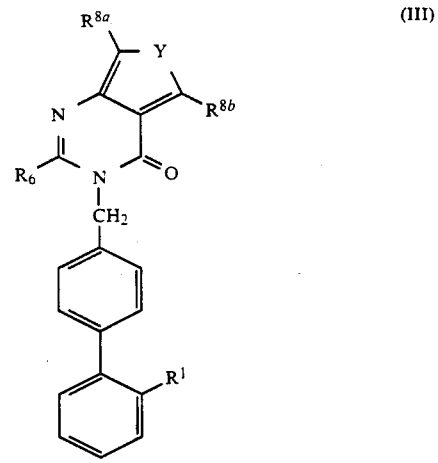

(III)

TABLE B

| Compound No. | R¹ | R⁶ | R⁸ᵃ | R⁸ᵇ | Y |
|---|---|---|---|---|---|
| B1 | —SO₂NHOH | Bu | Me | iPr | S |
| B2 | —SO₂NHSO₂Ph | Bu | Me | iPr | S |
| B3 | —SO₂NHSO₂Me | Pr | Me | Me | O |
| B4 | —SO₂NHSO₂-iPr | Pr | CO₂H | Me | S |
| B5 | (methyl-oxadiazole-sulfonyl, NH) | Bu | Me | Me | S |
| B6 | (methyl-triazole-N-Ph, S=O, NH) | Bu | Me | Me | S |

TABLE B-continued

| Compound No. | R¹ | R⁶ | R⁸ᵃ | R⁸ᵇ | Y |
|---|---|---|---|---|---|
| B7 | −NH−C(=O)−CO₂H | Pr | CO₂H | Me | S |
| B8 | −SO₂NHSO₂−iPr | Pr | Me | Ph | O |
| B9 | −SO₂NHP(=O)(O−CH₂Ph)₂ | Bu | Me | Me | S |
| B10 | [N-sulfonyl glycine ring: −N−CH₂−C(=O)−NH−S(O)₂−] | Bu | Me | Me | S |
| B11 | [isoxazoline with NHSO₂Ph] | Pr | Me | Me | S |
| B12 | [oxathiazole ring with NH, S(=O)₂] | Bu | Me | Me | S |
| B13 | −NHSO₂−(2-thienyl) | Bu | CO₂H | i-Pr | O |

Also exemplifying this subclass are the following compounds of the Formula IV shown in Table C:

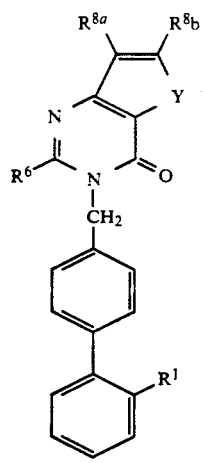

(IV)

TABLE C

| Compound No. | R¹ | R⁶ | R⁸ᵃ | R⁸ᵇ | Y |
|---|---|---|---|---|---|
| C1 | −SO₂NHOH | Bu | Me | iPr | S |
| C2 | −SO₂NHSO₂Ph | Bu | Me | iPr | S |
| C3 | −SO₂NHSO₂Me | Pr | Me | Me | O |
| C4 | −SO₂NHSO₂−iPr | Pr | CO₂H | Me | S |
| C5 | [heterocycle with N−O, N−S(O)₂] | Bu | Me | Me | S |
| C6 | [heterocycle with N−Ph, N−S=O] | Bu | Me | Me | S |
| C7 | −NH−C(=O)−CO₂H | Pr | CO₂H | Me | S |
| C8 | −SO₂NHSO₂−iPr | Pr | Me | Ph | O |
| C9 | −SO₂NHP(=O)(O−CH₂Ph)₂ | Bu | Me | Me | S |
| C10 | [N-sulfonyl glycine ring] | Bu | Me | Me | S |
| C11 | [isoxazoline−NHSO₂Ph] | Pr | Me | Me | S |
| C12 | [oxathiazole ring with NH, S=O₂] | Bu | Me | Me | S |
| C13 | −NHSO₂−(2-thienyl) | Bu | CO₂H | i-Pr | O |
| C14 | −NHSO₂−(2,4-difluorophenyl) | Bu | H | iPr | S |
| C15 | −SO₂NHCO₂Et | Bu | H | iPr | S |
| C16 | −SO₂NHCO₂i-Pr | Bu | H | iPr | S |
| C17 | −SO₂NHPO(OEt)₂ | Bu | H | iPr | S |

Another class of this embodiment are those compounds of Formula (I) wherein:

A—B—C together with the pyrimidinone to which it is attached form a member selected from the groups:

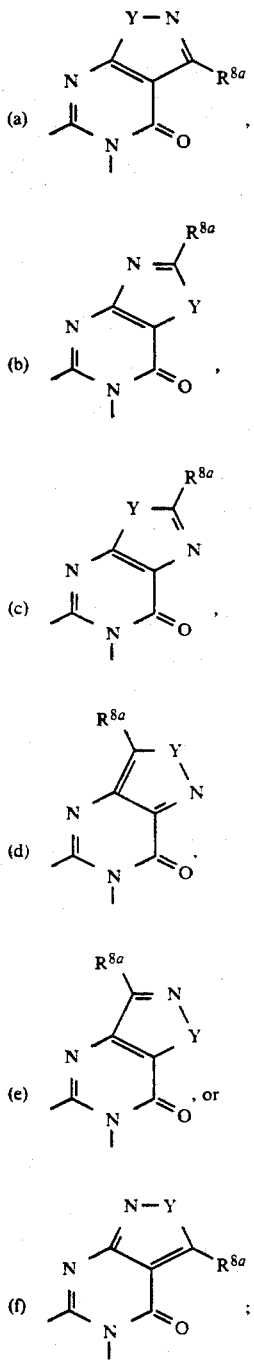

Y is O, S or NR$^7$;

R$^{2a}$, R$^{2b}$, R$^{3a}$, R$^{3b}$ are each independently H, C$_1$-C$_6$-alkyl; C$_2$-C$_6$-alkenyl, C$_2$-C$_6$-alkynyl, —Cl, —F, —NO$_2$, or —CF$_3$;

R$^6$ is C$_1$-C$_4$-alkyl, cyclopropyl, —CH$_2$CH$_2$CH$_2$CF$_3$, —CH$_2$CH$_2$CF$_3$, C$_2$-C$_5$-alkenyl, or cyclopropylmethyl;

R$^7$ is H or C$_1$-C$_6$ alkyl; and

R$^{8a}$ and R$^{8b}$ independently are: H, C$_1$-C$_4$-alkyl, —NO$_2$, —NR$^4$R$^{22}$, —OCH$_3$, —NR$^4$COOR$^{22}$, —Cl, CH$_2$COOR$^{4a}$, —S(O)$_x$—R$^{22}$, NR$^4$CONR$^4$R$^{22}$, CH$_2$OCO(C$_1$-C$_4$-alkyl), —NR$^4$COR$^{22}$, CO$_2$R$^{4a}$, —F, CH$_2$Ph, or —CONR$^4$R$^{22}$.

Exemplifying this subclass are the following compounds of the Formula V shown in Table D:

(V)

[Structure of Formula V]

TABLE D

| Compound No. | R$^1$ | R$^6$ | R$^{8a}$ | Y |
|---|---|---|---|---|
| D1 | —SO$_2$NHOH | Bu | Me | S |
| D2 | —SO$_2$NHSO$_2$Ph | Bu | Me | O |
| D3 | —SO$_2$NHSO$_2$Me | Pr | Me | O |
| D4 | —SO$_2$NHSO$_2$-iPr | Pr | CO$_2$H | S |
| D5 | [isoxazole sulfonamide structure] | Bu | Me | O |
| D6 | [thiadiazole N-Ph structure] | Bu | Me | O |
| D7 | —NH—C(O)—CO$_2$H | Pr | CO$_2$H | O |
| D8 | —SO$_2$NHSO$_2$-iPr | Pr | Me | S |
| D9 | —SO$_2$NHP(O)(O—CH$_2$Ph)$_2$ | Bu | Me | O |
| D10 | [cyclic sulfamide structure] | Bu | Me | O |
| D11 | [isoxazole NHSO$_2$Ph structure] | Pr | Me | O |

TABLE D-continued

| Compound No. | R¹ | R⁶ | R⁸ᵃ | Y |
|---|---|---|---|---|
| D12 | (structure: N-O-S(=O)₂-N-H ring with CH) | Bu | Me | O |
| D13 | -NHSO₂-(thiophene) | Bu | CO₂H | O |
| D14 | -NHSO₂-(2,4-difluorophenyl) | Bu | Me | S |
| D15 | -SO₂NHCO₂Et | Bu | Me | S |
| D16 | -SO₂NHCO₂i-Pr | Bu | Me | S |
| D17 | -SO₂NHPO(OEt)₂ | Bu | Me | S |

Also exemplifying this subclass are the following compounds of the Formula VI shown in Table E:

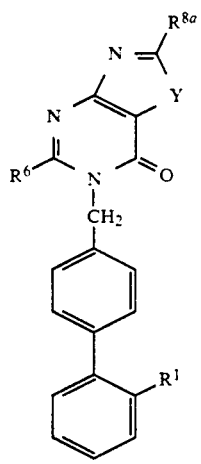

(VI)

TABLE E

| Compound No. | R¹ | R⁶ | R⁸ᵃ | Y |
|---|---|---|---|---|
| E1 | -SO₂NHOH | Bu | Me | S |
| E2 | -SO₂NHSO₂Ph | Bu | Me | S |
| E3 | -SO₂NHSO₂Me | Pr | Me | S |
| E4 | -SO₂NHSO₂-i-Pr | Pr | Me | O |
| E5 | (structure: N-O-S(O)₂-N-H ring) | Bu | Me | O |
| E6 | (structure: N-N-Ph, N-S=O ring) | Bu | Me | O |
| E7 | -NH-C(=O)-CO₂H | Pr | Me | S |
| E8 | -SO₂NHSO₂-i-Pr | Pr | Me | S |
| E9 | -SO₂NHP(=O)(O-CH₂Ph)₂ | Bu | Me | S |
| E10 | (structure: N-S(O₂)-N-H ring with C=O) | Bu | Me | O |
| E11 | (structure: N-O ring with NHSO₂Ph) | Pr | Me | S |
| E12 | (structure: N-O-S(=O)₂-N-H ring) | Bu | Me | S |
| E13 | -NHSO₂-(thiophene) | Bu | i-Pr | O |
| E14 | -NHSO₂-(2,4-difluorophenyl) | Bu | iPr | S |
| E15 | -SO₂NHCO₂Et | Bu | iPr | S |
| E16 | -SO₂NHCO₂i-Pr | Bu | iPr | S |
| E17 | -SO₂NHPO(OEt)₂ | Bu | iPr | S |
| E18 | -SO₂NHSO₂i-Pr | Pr | Pr | N—CH₃ |
| E19 | -SO₂NHCO₂Et | Bu | Bu | N—CH₃ |

ABBREVIATIONS USED IN SCHEMES

| | |
|---|---|
| DMAP | Dimethylaminopyidine |
| -OTs | p-Toluenesulphonate |
| -OTf | Trifluoromethanesulfonate |
| DMF | Dimethylformamide |
| DBU | 1,8-Diazabicyclo[5.4.0]undecane |
| FABMS | Fast Atom bombardment mass spectroscopy |
| THF | Tetrahydrofuran |
| DMSO | Dimethylsulfoxide |
| EtAc | Ethyl acetate |
| HOAc | Acetic Acid |
| TFA | Trifluoroacetic acid. |

References Cited In Schemes

1 *The Chemistry of Heterocyclic Compounds-Fused Pyrimidines*, Part 1-The Quinazolines, W. L. F. Armarego, Interscience Publishers, New York, 1967
2 "Quinazolines"., W. L. F. Armarego, *Adv. in Het Chem.*, Vol 24, Pg 1, 1979.

3 For pyrroles: R. Boehm, R. Pech, *Pharmazie*, 245, 1990.
4 For pyrazoles: C. C. Cheng, R. K. Robins, *J. Org. Chem.*, 191, 1958.
5 For furan: S. S. Sangapure, Y. S. Agasimudin, *J. Ind. Chem.* 627, 1978.
6 For pyrazoles and thiophenes: Smithkline Beckman Corp EP- 349-239-A.
7 For thiophenes: C. J. Shishoo, M. B. Devani, K. S. Bhadti, S. Mohan, L. T. Patel, *Indian J. Chem.*, 1039, 1989.
8 For isothiazolo{5,4-d}pyrimidinone: S. Rujappa, B. G. Advani, R. Speenivsain., *Ind. J. Chem.*, 391, 1976.
9 For thiophene, furan, pyrrole: K. G. Dave, C. J. Shishov, M. B. Devani, R. Kalyanaraman, S. Ananthan, G. V. Ullas, V. S. Bhadti, *J. Het. Chem.*, 1497, 1980.
10 For purines: A. Yamazaki, I. Kumashiro, T. Takenishi, *J. Org. Chem.*, 3258, 1967.
11 For isothiazolo{4,5-d} and {4,3-d}pyrimidinone: A Holland, R. Slack T. F. Warren, D. Buttimore, *J. Chem. Soc.* 7277, 1965.
12 For pyrazoles: R. Bohm, *Pharmazie*, 45, 282, 1990.
13 For thiophene: M. S. Manhas, S. D. Sharma, S. G. Amin, *J. Med. Chem.* 106, 1971.
14 For purines: *Comprehensive Heterocyclic Chemistry*, A. R. Katrizky and C. Rees. Volume 5, Pg 567.
15 For purines: Bergman and Tumari, *J. Chem Soc.* 4468, 1961.
16 For purines: *Heterocyclic Compounds, Fused Pyrimidines*, Part 2-purines by J. H. Lister. Wiley-Interscience, New York, 1971.
17 For purines: E. Richter, J. E. Loeffler, E. C. Taylor, *J. Am. Chem. Soc.*, 3144, 1959.
18 For furans: J. P. Marquet, J. A. Louisfert, E. Bisagni. *Bull Soc. Chim, France*, 4344, 1969.
19 *Chem Scripta*, 135, 1981.
20 For pyrroles: T. Murata, T. Sugawara, K. Ukawa., *Chem. Pharm. Bull.*, 26, 3083, 1978.
21 For oxazolo{5,4-d}pyrimidin-7(6H)-ones: V. D. Patil, L. B. Townsend, *J. Het. Chem.*, 503, 1971.
22 For oxazolo (4,5-d) pyrimidin-7(6H)-ones: M. Sekiya, J. Suzuki., *Chem Pharm Bull.*, 2242, 1970.

The compounds of Formula (I) can be synthesised using the reactions and techniques described below. The reactions are performed in a solvent appropriate to the reagents and materials employed and suitable for the transformation being effected. It is understood by those skilled in the art of organic synthesis that the functionality present on the heterocycle and other parts of the structure should be consistent with the chemical transformations proposed. Depending upon the reactions and techniques employed, this may involve changing the order of the synthetic steps, the use of required protecting groups followed by deprotection and, depending upon the particular pyrimidinone fused heterocycle being formed, the use of different strategies may be employed regarding the cyclization steps and the particular starting materials utilized.

General information on the synthesis of quinazolinones may be found in several reference works. [1,2] Much of the chemical properties of the quinazolinone structural class may be applied to the preparation and modification of compounds of Formula (I).

The preparation of the pyrimidin-4(3H)-ones (2) fused to a desired heterocycle where E is a single bond may be achieved via several methods (Scheme 1) Treatment of a vicinally substituted amino nitrile such as (3) with an acid chloride, tertiary base and acyl chloride will give an amide. Hydrolysis of the nitrile with basic hydrogen peroxide will give, following heating, the desired pyrimidinone heterocycle (2)[3,4,5]. Alternatively, when a vicinally substituted amino ester or carboxylic acid (4) is treated with an imidate ester under acidic or basic conditions, conversion to the pyrimidinone (2) occurs. [6,7,8,9] Furthermore, vicinally substituted amino amides such as (5) may be condensed with an orthoacetate to give (3) [10,11].

SCHEME 1

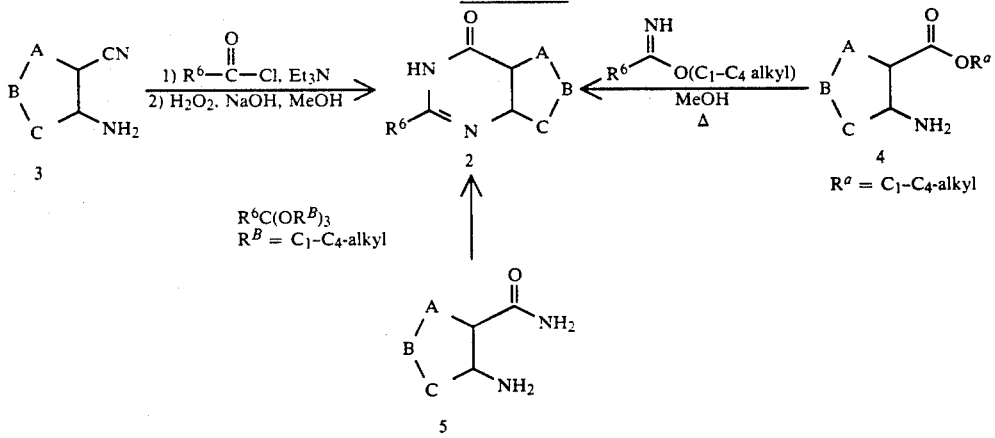

The preparation of compounds of Formula (I) may be achieved through the alkylation of the heterocycle (3) under appropriate basic conditions with a benzylic halide (6) (Scheme 2). The method used in any particular system will depend on the heterocycle in question, whether it is protected or not and the state of functionalization of the heterocycle. The choice of alkylative conditions will depend also on the particular regiochemistry of alkylation on the heterocycle. Changes in solvent, base, temperature and overall reaction methodology may control the observed alkylating regiochemistry. The $R^{1a}$ moiety illustrated in Scheme 2 and subsequent schemes represents a precursor group of $R^1$, which optionally may contain a protecting group. Any protecting groups on the $R^{1a}$ moiety can be removed under appropriate conditions. Alternatively, the $R_1$ group may be constructed from $R^{1a}$ using techniques known to those skilled in the art.

SCHEME 2

(d) when $R^{1a}$ contains a t-butyl or triphenylmethyl protecting group, it is treated with trifluoroacetic acid or HCl/MeOH

SCHEME 3

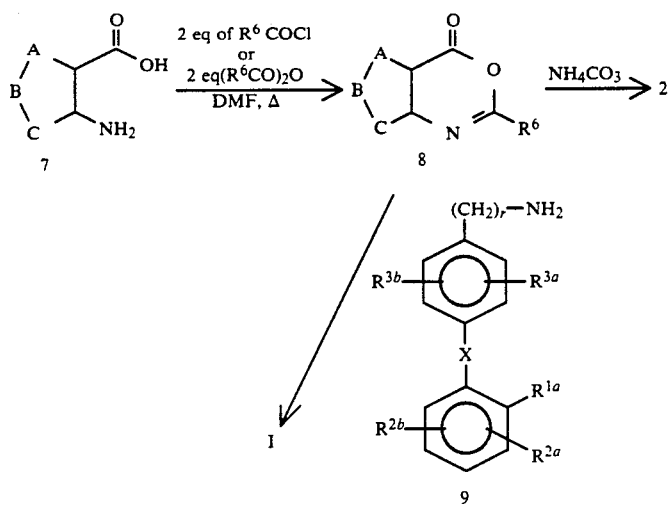

In cases where r=1 or 2 the method described above may not be suitable due to elimination or lack of reactivity. As an alternative (Scheme 3), a vicinal amino carboxylic acid (7) may be treated with two equivalents of an acylating reagent in a polar aprotic solvent in the presence of a tertiary amine base to give, after heating, the benzoxazine (8). (12,,13) Addition of an amine of general formula (9) and heating in the presence or absence of base will give the product of formula (I) after appropriate deprotection. Furthermore, addition of solid ammonium carbonate to the reaction mixture in place of the amine (9) will give rise to the pyrimidinone (2).

The benzyl halides (6) including the more preferred alkylating agents (6a and 6b, Scheme 4) can be prepared as described in European Patent Applications 253,310 and 291,969 and the references cited therein. However, a preferred method to prepare the biphenyl precursors (10a), (10b) and (10c) using Ni(O) or Pd(O) catalyzed cross-coupling reaction [E. Negishi, T. Takahashi, and A. O. King, Org. Synthesis, 66, 67 (1987)] is outlined in Scheme 4. As shown in Scheme (4), treatment of 4-bromotoluene (11) with t-BuLi, followed by the addition of a solution of $ZnCl_2$, produces the organo-zinc compound (12). Compound (12) is then coupled with (13a) or (13b) in the presence of $Ni(PPh_3)_2Cl_2$ catalyst to produce the desired biphenyl compound 10a or 10b ($PPh_3$=triphenylphosphine). Similarily, 1-iodo-2-nitrobenzene (13c) is coupled with organo-zinc compound (12) in the presence of $Pd(PPh_3)_4$ catalyst [prepared by treating $Cl_2Pd(PPh_3)_2$ with $(i-Bu)_2AlH$ (2 equiv.)] to give the biphenyl compound (10c). These precursors, (10a), (10b) and (10c), are then transformed into halomethylbiphenyl derivatives (6a), (6b) and (6c), respectively, according to procedures described in European Patent Applications 253,310 and 291,969.

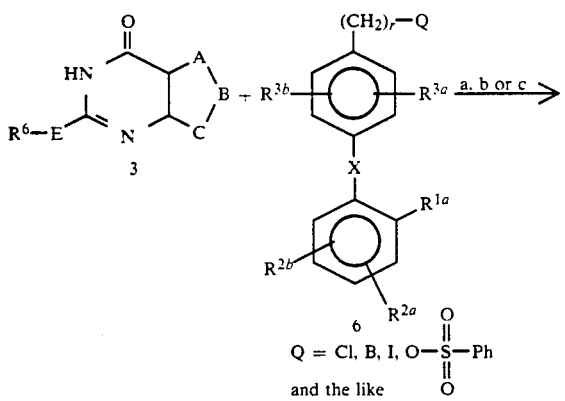

Q = Cl, B, I, O—S(=O)(=O)—Ph and the like

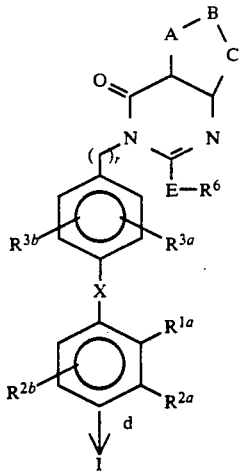

(a) NaH, 6, DMF
(b) $K_2CO_3$, acetone, PTC, 6
(c) i) TMSNHTMS
  ii) 6

SCHEME 4

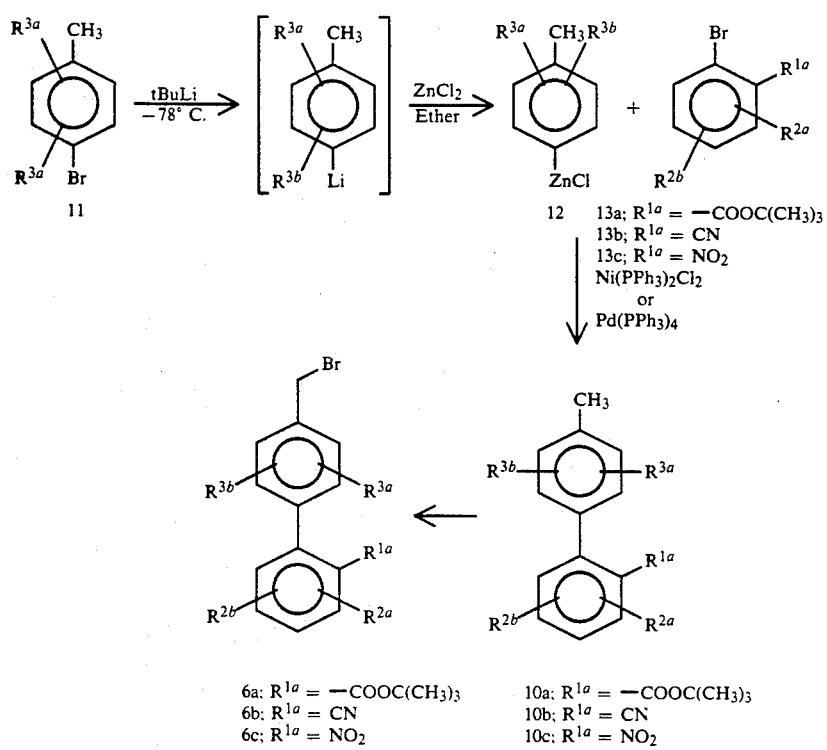

When there is additional substitution on the second phenyl ring ($R^{2a}$, $R^{2b}$ are not equal to hydrogen) the preferred method to prepare the biphenyl precursors (10d) and (10e), using the Pd(0) catalyzed cross-coupling reaction [J. K. Stille, *Angrew, Chem. Int. Ed. Engl.*, (25), 508 (1986)], is outlined in Scheme 5. As shown in Scheme 5, p-tolyltrimethyltin (14) is coupled with (13d) or (13e) in refluxing toluene in the presence of 5 mole % of Pd(PPh$_3$)$_4$ to produce the desired biphenyl compounds 10d and 10e. Table I illustrates the synthetic utility of this protocol. Compounds 10d ($R^2$=NO$_2$) and 10e ($R^2$=NO$_2$) could be converted to their respective chlorides by catalytic hydrogenation, diazotization and treatment with copper (I) chloride. The biphenyl fluorides which could not be obtained by direct coupling to a fluoro arylbromide were prepared from (10d) ($R^2$=NO$_2$) and (10e) ($R^2$=NO$_2$) via reduction, formation of the diazonium tetrafluoroborate salt and thermal decomposition. These precursors (10d) ($R^2$=NO$_2$ or F or Cl) and 10e ($R^2$=NO$_2$ or F or Cl) are then transformed into the halomethyl biphenyl derivatives (6d) and (6e), respectively according to the procedures described in European Patent Applications 253,310 and 292,969.

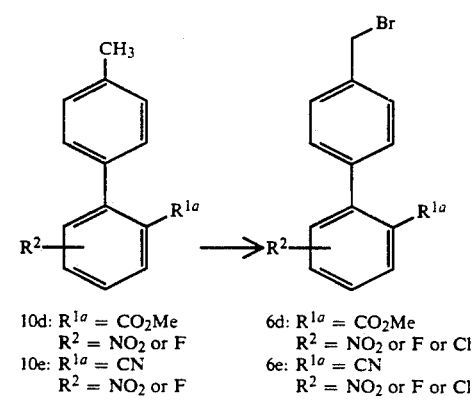

TABLE I
Biphenyl Synthesis

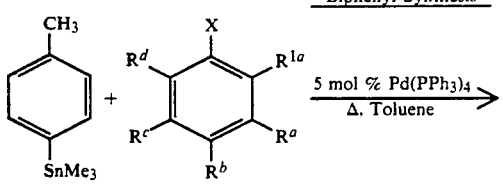

(13d, 13e)

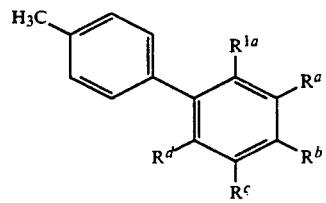

(1od, 10e)

| X  | $R^{1a}$ | $R^a$ | $R^b$ | $R^c$ | $R^d$ | Product ($R^a$) | Rf (solvent) | Yield |
|----|----------|-------|-------|-------|-------|-----------------|--------------|-------|
| Br | $CO_2Me$ | $NO_2$ | H | H | H | 10d (3'-nitro) | 0.35(15:1 Hex/EtOAc) | 71% |
| Br | CN | H | $NO_2$ | H | H | 10e (4'-nitro) | 0.62(2× 6:1 Hex/EtOAc) | 74% |
| Br | $CO_2Me$ | H | F | H | H | 10d (4'-fluoro) | 0.43(15:1 Hex/EtOAc) | 83% |
| Cl | $CO_2Me$ | H | H | $NO_2$ | H | 10d (5'-nitro) | 0.22(15:1 Hex/EtOAc) | 70% |
| Br | $CO_2Me$ | H | H | H | $NO_2$ | 10d (6'-nitro) | 0.24(15:1 Hex/EtOAc) | 79% |
| Br | CN | H | F | H | H | 10e (4'-fluoro) | 0.44(15:1 Hex/EtOAc) | 64% |
| Cl | CN | H | H | F | H | 10e (5'-fluoro) | 0.40(15:1 Hex/EtOAc) | 62% |

Compounds of formula I where $R^1$ is

    35 may be prepared from the corresponding carboxylic acid derivatives (15) as outlined in Scheme 6. The carboxylic acid (15), obtained as described in Schemes 2 and 3, can be converted into the corresponding amide by treatment with carbonyldiimidazole and then with ammonia. The resulting amide then can be treated with sodium hydride or n-butyllithium in THF at $-20°$ C. followed by an appropriately substituted phosphonyl or phosphinyl halide to form the desired compounds (15a).

SCHEME 6

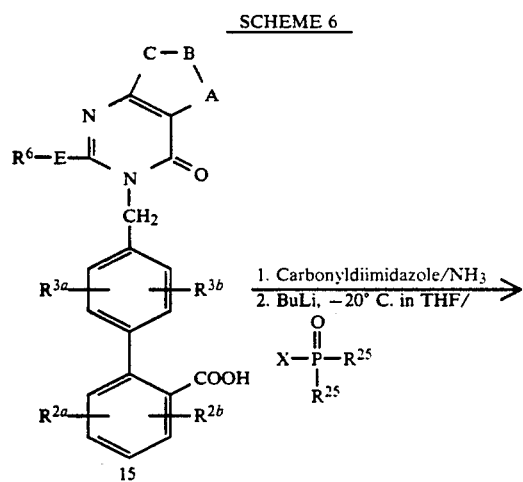

-continued
SCHEME 6

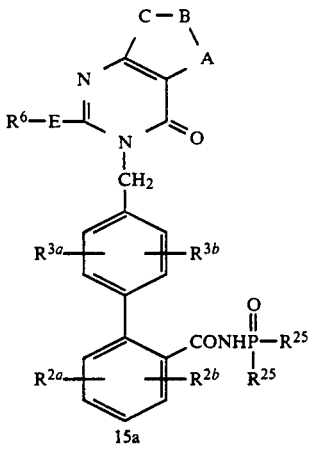

The biaryl sulfonamides (21) and (26), precursors for the alkylating agent 22, can be prepared from appropriate aryl-organotin precursors using palladium(0) catalyzed cross-coupling reactions [J. K. Stille, Pure Appl. Chem., 57, 1771 (1985); T. R. Baiely, Tetra Lett., 27, 4407 (1986); D. A. Widdowson and Y. Z. Zhang, Tetrahedron, 42, 2111 (1986)], as outlined in Schemes 7 and 8. The organotin compound (18) [S. M. Moerlein, J. Organometallic Chem., 319, 29 (1987)], obtained from the aromatic precursors (16 or 17), may be coupled with aryl sulfonamide (20) using Pd(PPh$_3$)$_4$ or (PPh$_3$)$_2$PdCl$_2$ as catalysts to give biaryl sulfonamide 21. Similarly, the biphenylmethyl bromide (22) may be alternatively prepared from the appropriate organotin precursor (25) using the Pd(0) catalyzed cross-coupling reaction as outlined in Scheme 8.

SCHEME 7

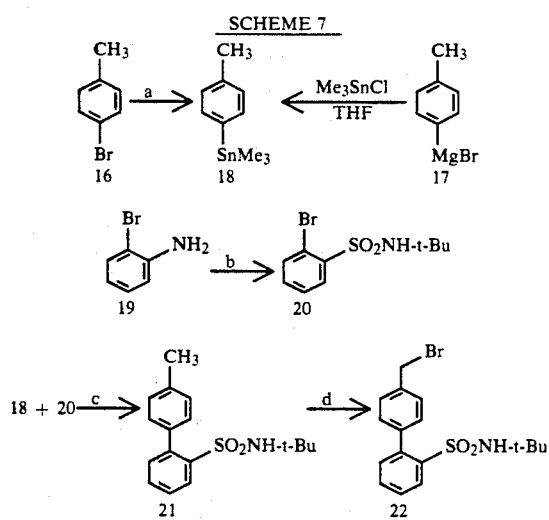

a. i) t-BuLi/ether, −78° C. ii) Me₃SnCl
b. i) NaNO₂/HCl ii) SO₂, CuCl₂ (iii) t-butylamine
c. Pd(PPh₃)₄, Toluene or (PPh₃)₂PdCl₂, DMF, Heat
d. NBS/CCl₄, AIBN, Reflux

SCHEME 8

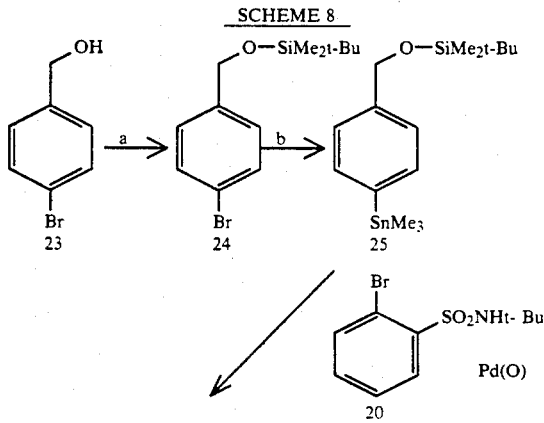

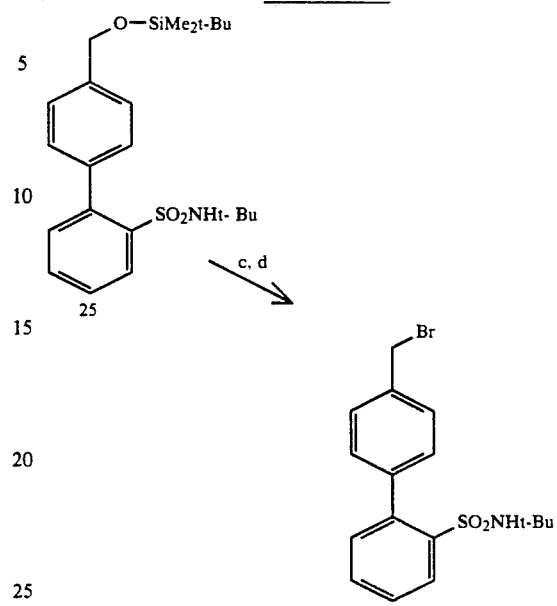

a. t-BuMe₂Si—Cl/Imidazole, DMF
b. t-BuLi, −78° C., Me₃SnCl
c. Tetrabutylammonium fluoride
d. CBr₄/Ph₃P.

Compounds of formula I where $R^1$ is —SO₂N-HSO₂R²³ may be prepared from the key sulfonamide intermediate 27 as outlined in Scheme 9. The intermediate 27 may be prepared by the alkylation of appropriate heterocycles with the alkylating agent 22 as outlined in Scheme 1. Treatment of 27 with trifluoroacetic acid followed by acylation of the resulting sulfonamide 28 with appropriate sulfonyl chlorides may produce the desired compounds (29).

SCHEME 9

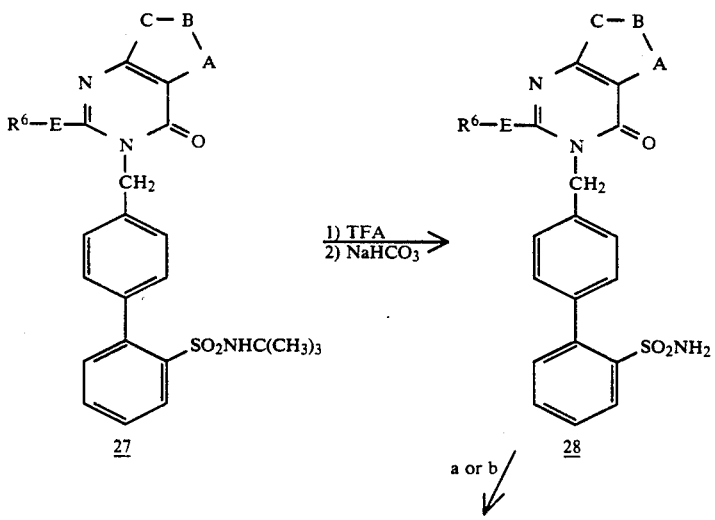

SCHEME 9

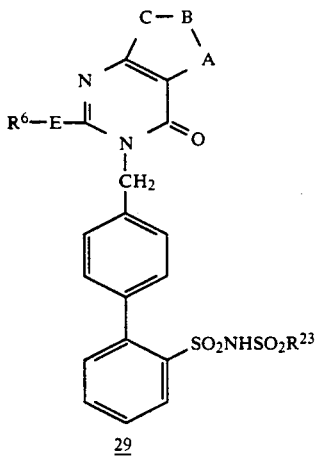

a. i) NaH/THF or DMF (ii) $R^{23}SO_2Cl$
b. $R^{23}SO_2Cl$, DBU, THF

Compounds of Formula (I) wherein $R^1$ is —$SO_2NH$-$CO_2R^{23}$ may be prepared by reacting an appropriate chloroformate with the sulfonamide (28) in pyridine or in the presence of DBU in THF to afford the desired compound (30), as outlined in Scheme 10.

SCHEME 10

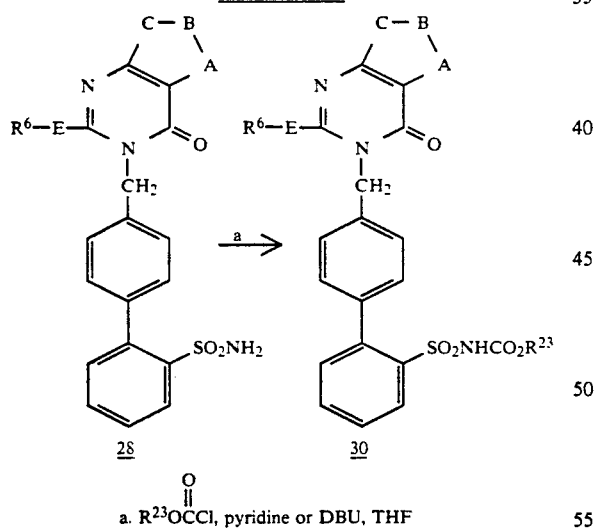

a. $R^{23}OCCl$, pyridine or DBU, THF

Compounds of Formula (I) wherein $R^1$ is

may be prepared by treating sulfonamide (28) with n-butyllithium in THF followed by the treatment of the resulting anion with an appropriately substituted phosphonyl or phosphinyl halide to form the desired compounds (13). (Scheme 11)

SCHEME 11

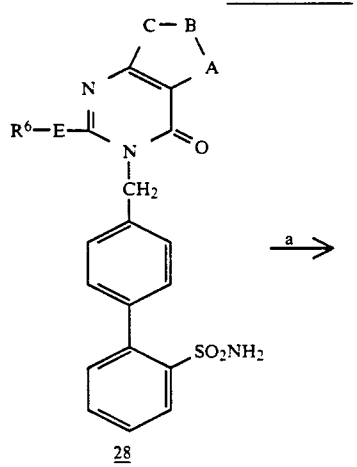

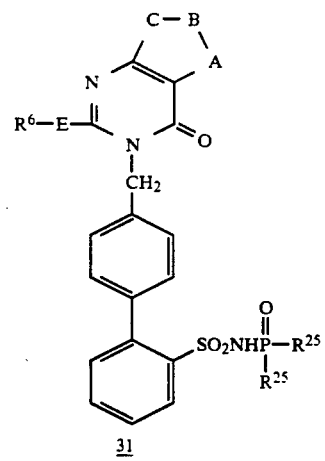

a. BuLi, −20° C. in THF/X—$\overset{\overset{O}{\|}}{\underset{R^{25}}{P}}R^{25}$ Compounds of Formula (I) wherein R¹ is SO₂N-HSO₂N(R⁴)(R⁹) or

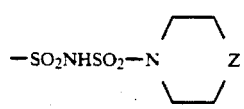

may also be prepared from sulfonamide (28) as outlined in Scheme 12. Treatment of 28 with n-butyllithium in THF at −25° C. and then with an appropriate sulfamoyl halide may produce the desired product (32) or (33).

SCHEME 12

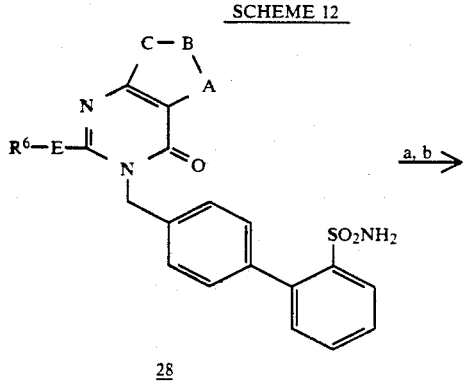

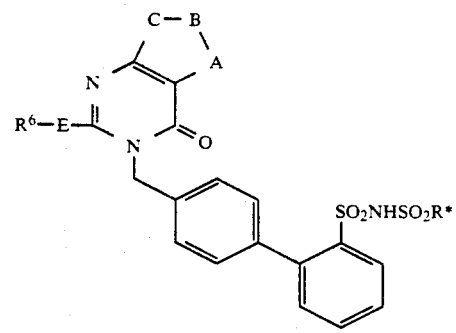

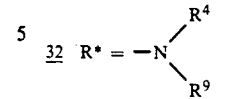

a. nBuLi, −25° C. in THF
b. R* SO₂Cl

Compounds of Formula (I) wherein R¹ is —NH-SO₂NHSO₂R²³ or

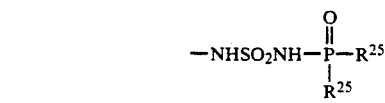

may be prepared from arylamine (35) as outlined in Scheme 13. The arylamine (35) obtained from the corresponding nitro compound 34 can be treated with t-butylsulfamoyl chloride to afford the protected amino sulfonamide (36). The amino sulfonamide (37) obtained after removal of the t-butyl protecting group may then be reacted with an appropriate acylating agent in the presence of a base such as pyridine or DBU in an organic solvent such as THF or DMF to form the desired products (38a) or (38b).

Compounds of the Formula (I) wherein R¹ is —NH-SO₂R²³ may be prepared by the reaction of an appropriate sulfonyl halide (R²³SO₂Cl) or sulfonyl imidazole derivative with the aryl amine 35 in the presence of an appropriate base such as pyridine, triethylamine or DBU.

SCHEME 13

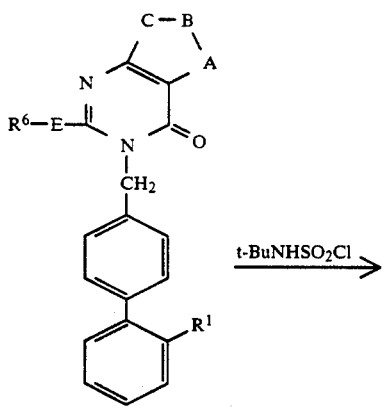

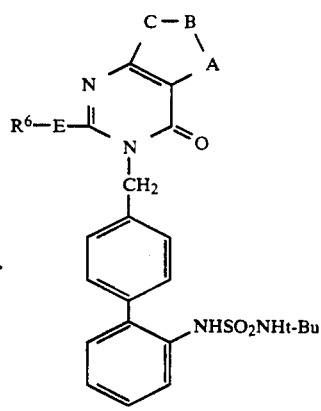

SCHEME 13

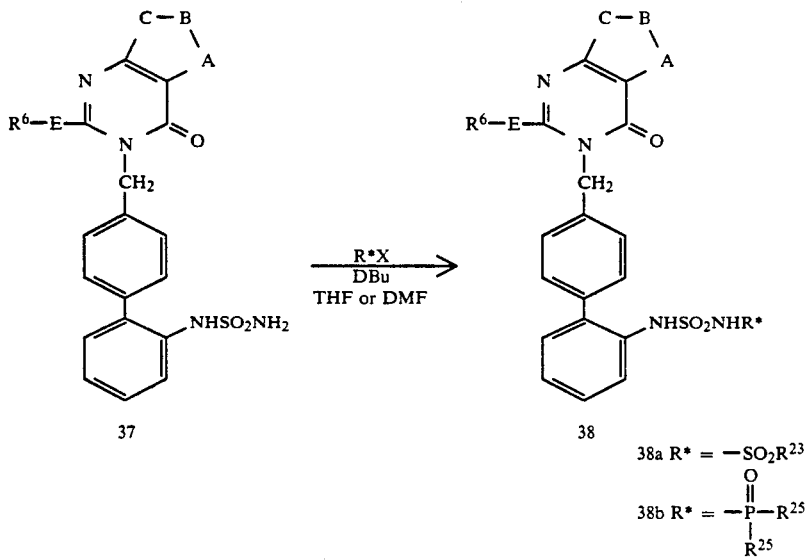

38a R* = —SO₂R²³

38b R* = —P(=O)(R²⁵)R²⁵

Compounds of Formula (I) and the benzyl halides of the formula (44) wherein R¹ is 1,2,3,5-oxathiadiazole-2-oxide may be prepared from the corresponding cyano derivative (39) or cyano precursor (10b) as outlined is Schemes 14 and 15, respectively utilizing procedures described in U.S. Pat. No. 4,910,019. The cyano derivatives (39), obtained as described in Scheme 1, can be converted into the corresponding amidoxime (40) by treatment with hydroxylamine hydrochloride and sodium methoxide in an organic solvent, such as methanol or DMSO. The amidoxime (40) then can be treated with base and thionyl chloride in an aprotic solvent to form the desired 1,2,3,5-oxathiadiazole-2-oxide (41). Similarly, the oxathiadiazole-2,2-dioxide 42 can be prepared by treatment of amidoxime 40 with a base and sulfuryl chloride. As shown in Scheme 15, the cyano precursor (10b) may be converted into the desired 1,2,3,5-oxathiadiazole (44) which is then protected with the trityl group prior to the formation of the desired benzyl halide (45). The protecting group is removed subsequent to the alkylation of heterocycle (1) to give the desired product (41).

SCHEME 14

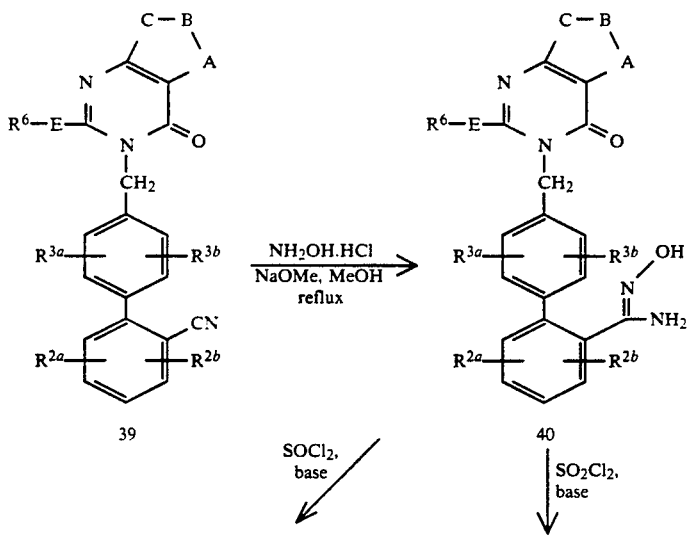

SCHEME 14

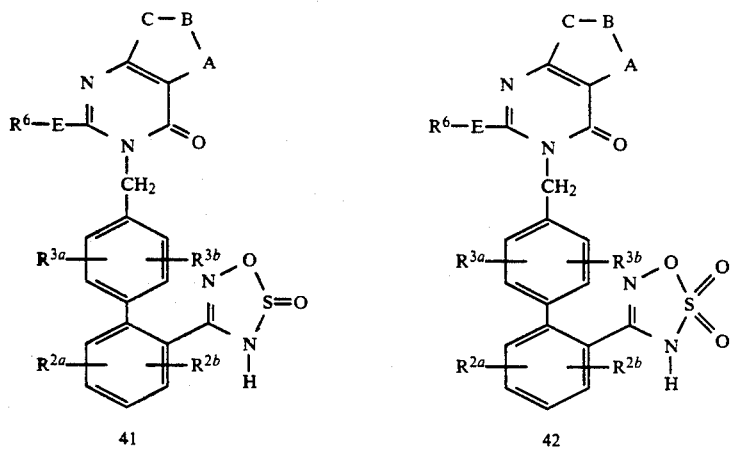

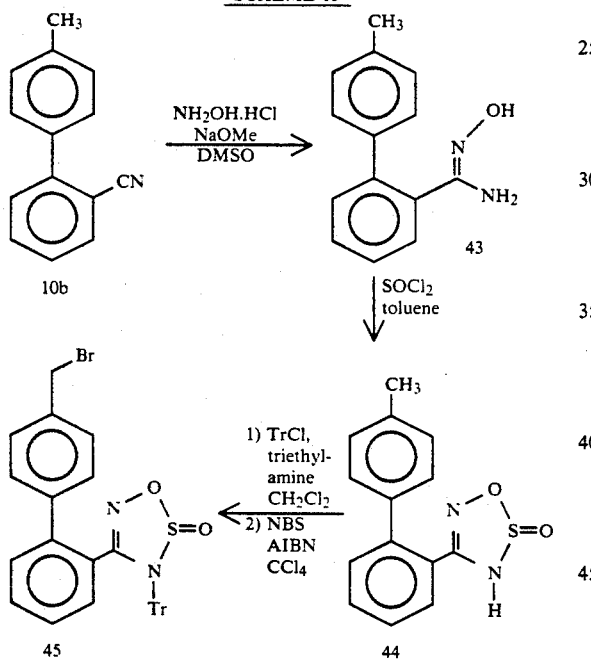

SCHEME 15

Compounds of Formula (I) and the benzyl halides of the formula (3) wherein $R^1$ is 1,2,3,5-thiatriazole-1-oxide may be prepared from the corresponding precursors 46 or 51 as outlined in Schemes 16 and 17, respectively. Intermediate 51 may be prepared from the biphenyl 10a according to the scheme illustrated (see procedures in U.S. Pat. No. 4,870,186). Intermediates (47) and (52) can be treated with $SOCl_2$ (see procedures in: Ber. Deutsch. Chem. Ges. 1971, 104 pp 639) to give intermediates, (48) and (53). Bromination of the N-protected compounds (49) and (53) provides intermediates 50 and 54 respectively. After alkylation with an appropriate heterocycle, the trityl group of the intermediate derived from 50 is removed with protic acid and the cyanoethyl group of the intermediate derived from 54 is removed upon treatment with hydroxide. Alternatively, (50) and (54) may be prepared as shown in Scheme 18 and 19. Treatment of (55) with $SOCl_2$ (see procedures in: Ber. Deutsch. Chem. Ges. 1971, 104 pp 639) provides (56), which under mild hydrolytic conditions provides (48). The conversion of (48) to (50) is as described for Scheme 16. Alkylation of the trityl protected analog (57) by treatment with a base such as NaH and an alkyl halide would provide (49), which then may be converted to (54) as previously described.

SCHEME 16

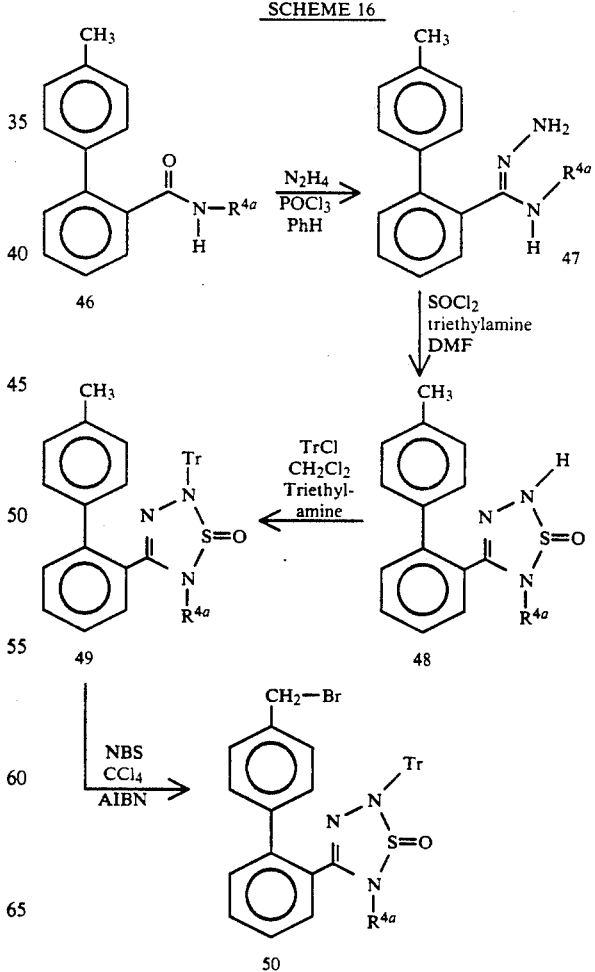

SCHEME 17
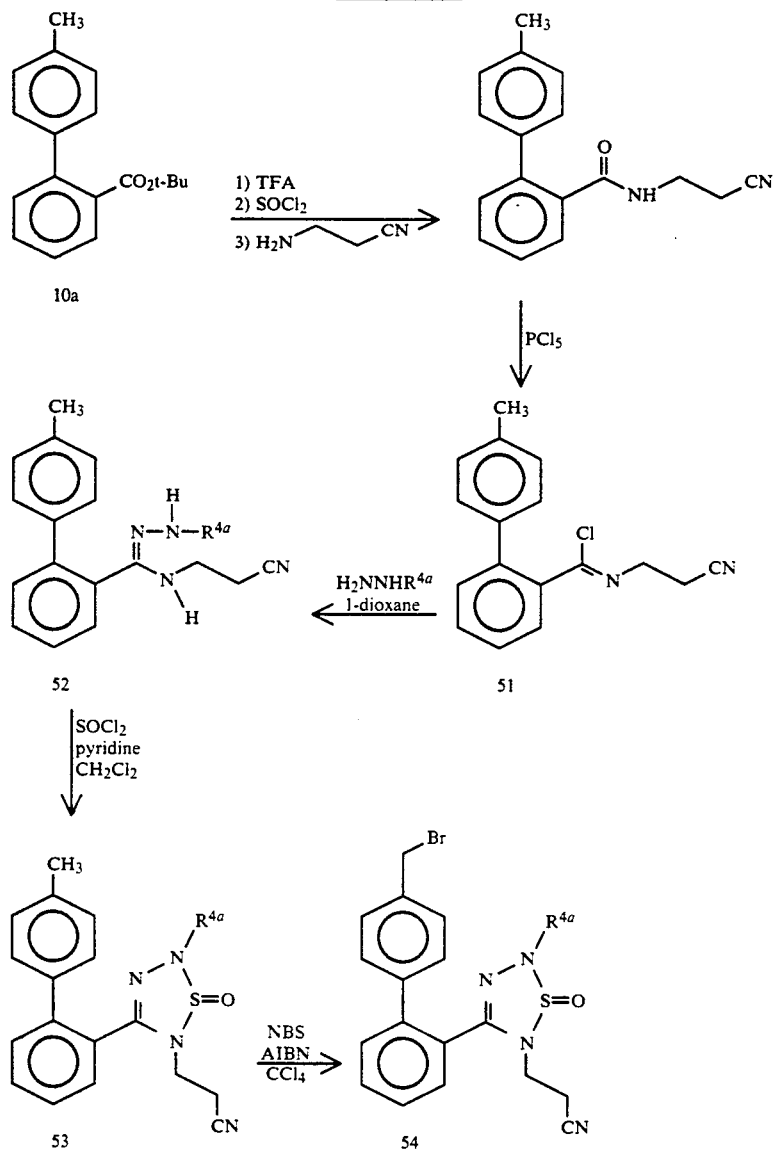
SCHEME 18
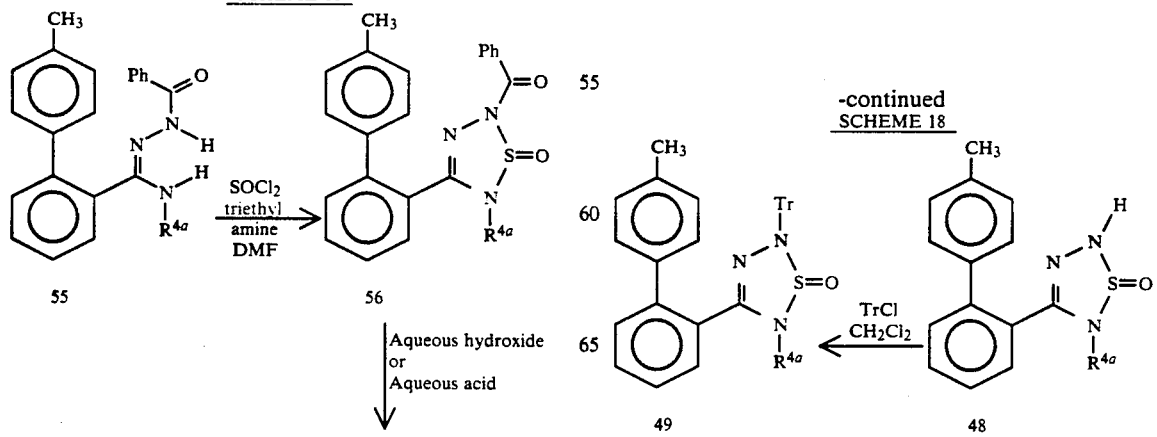

-continued
SCHEME 18

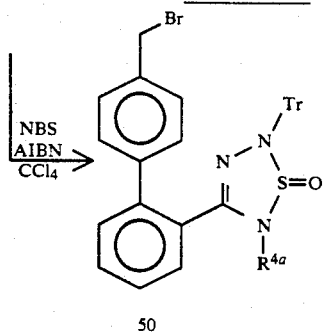

50

SCHEME 19

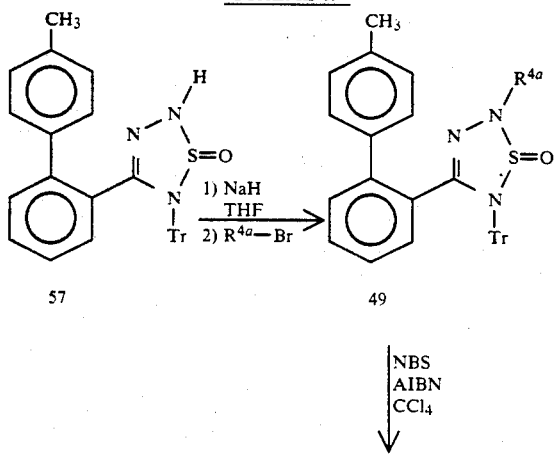

57    49

|NBS
|AIBN
|CCl₄
▼

-continued
SCHEME 19

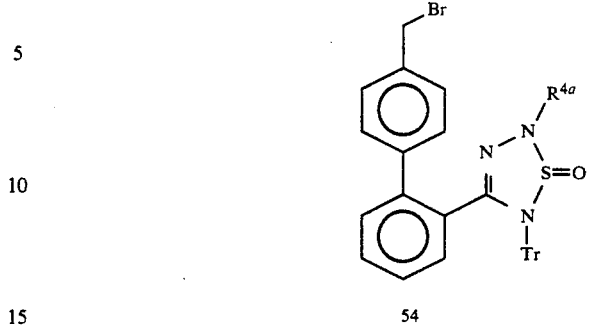

54

Compounds of Formula (I) and the benzyl halides of formula (6) wherein $R^1$ is 1,2,3,5-thiatriazole-1,1-dioxide-4-yl may be prepared using procedures described in *Monatsh. Chem.*, 1985, 116, pp 1321 and described herein. Sequential treatment of intermediates such as (51) or (47) with n-BuLi and $SO_2F_2$ will provide the 1,2,3,5-thiatriazol-1,1-dioxide analogs of (48) and (52). Further elaboration of the afore mentioned analogs by the methods described for the conversion of (48) to (50) in Scheme 16 and the methods described for the conversion of (52) to (54) in Scheme 17 would give the benzyl halides of formula (2) wherein $R^1$ is 2-triphenylmethyl-1,2,3,5-thiatriazole-1,1-dioxide-4-yl and 5-triphenylmethyl-1,2,3,5-thiatriazole-1,1-dioxide-4-yl, respectively.

Compound of Formula (I) wherein $R^1$ is 3-oxo-1,2,4-thiadiazolidine-1,1-dioxide may be prepared from the nitro derivative (10c) as outlined in Scheme 20. The amino compound 58 obtained from 10c may be reacted with t-butyl sulfamoylchloride to form the intermediate 59, which then can be alkylated with an appropriate bromoacetic acid derivative to give 60. Treatment of 60 with trifluoroacetic acid followed by the treatment with an appropriate base such as sodium or potassium alkoxide may produce the desired compound 61, which can be elaborated further to give the key alkylating agent 63 as outline in the scheme. Alkylation of an appropriate heterocyclic compound with 63 may then furnish the desired antagonist.

SCHEME 20

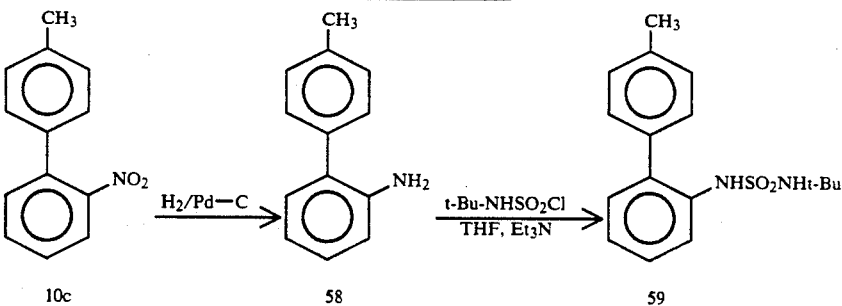

SCHEME 20

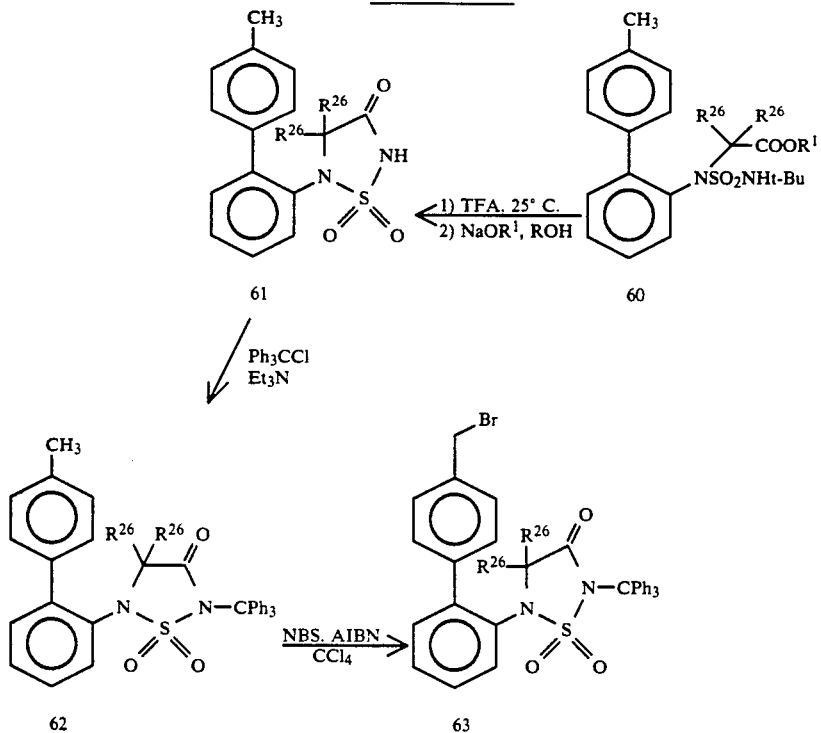

Compound of Formula (I) wherein $R^1$ is 5-aminosulfonyl-1,2,4-oxadiazole may be prepared using the bromomethyl biphenyl derivative 67 and an appropriate heterocyclic compound. The synthesis of 67 can be accomplished as outlined in Scheme 21. The amidoxime 43 may be reacted with S-methylisothiourea to form the 5-amino-1,2,4-oxadiazole 64, which can be then treated with an appropriate sulfonylchloride to give the corresponding 5-aminosulfonyl-1,2,4-oxadiazole 65. The appropriately protected derivative 66 then can be brominated to form the desired alkylating agent 67.

SCHEME 21

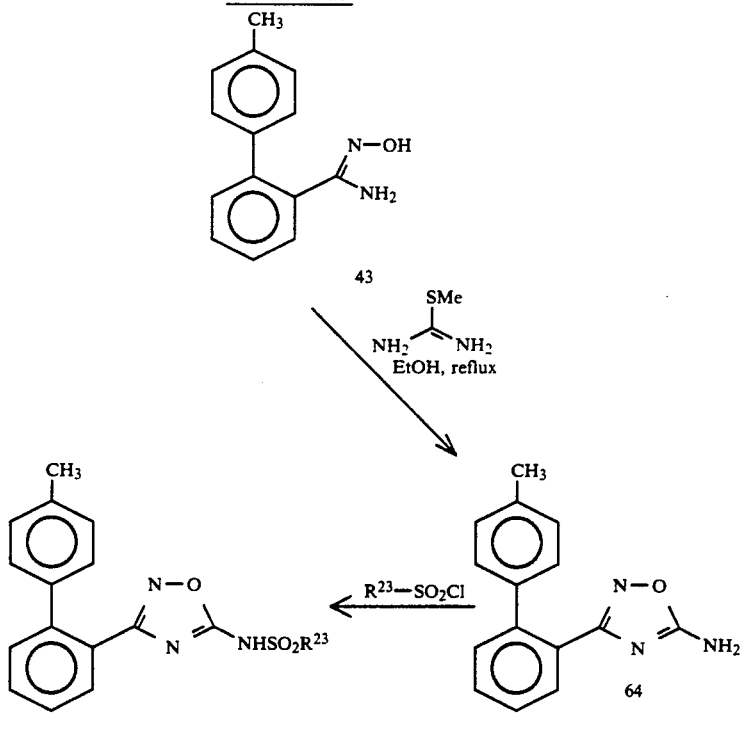

SCHEME 21

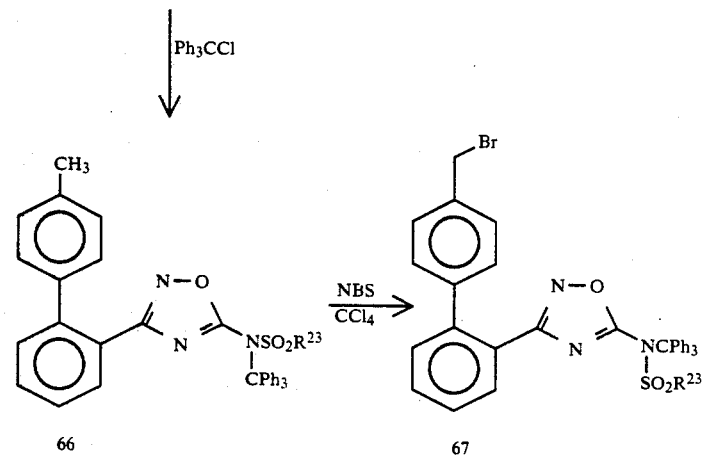

Compounds of Formula (I) wherein $R^1$ is 3-aminosulfonyl-1,2,4-oxadiazole can be prepared starting from the carboxylate derivative (10a) as outlined in Scheme 22. The ester derivative 68 obtained from 10a is treated with N-hydroxy guanidine sulfate in the presence of an alkoxide base to form the 3-amino-1,2,4-oxadiazole derivative 69, which may be reacted with an appropriate sulfonyl chloride to give the 3-aminosulfonyl-1,2,4-oxadiazole compound 70. The compound 71 can be prepared from 70 as outlined in Scheme 22.

SCHEME 22

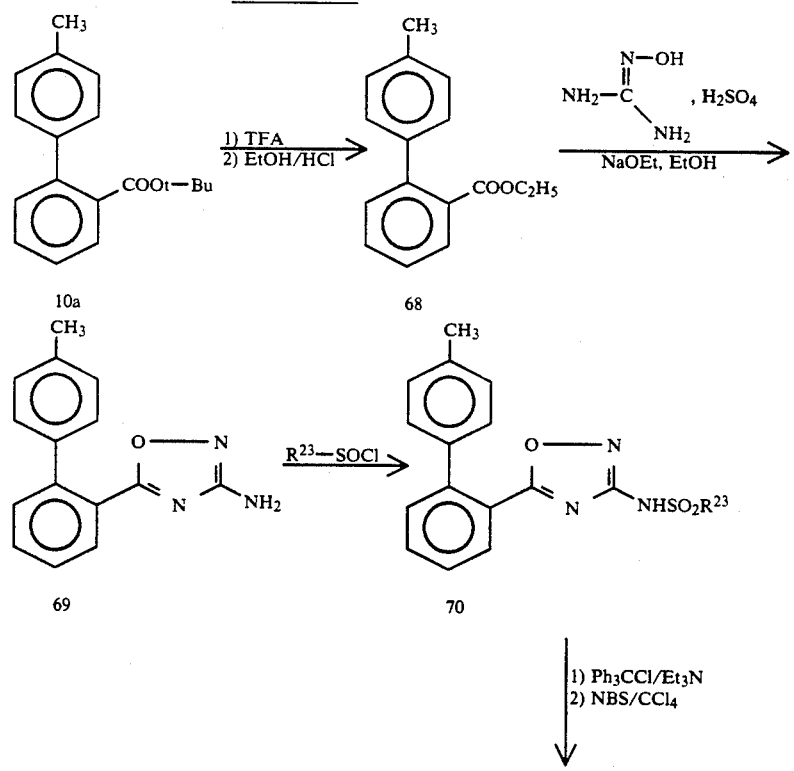

SCHEME 22

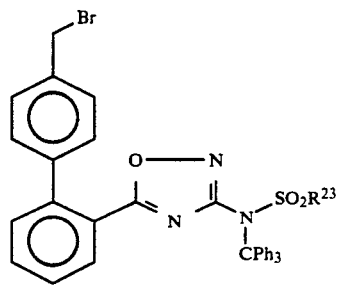

71

20

Compounds of Formula (I) and the benzyl halides of formula (2) wherein R¹ is 1,2,3-oxathiazin-4(3H)-one-2,2-dioxide-6-yl may be prepared as outlined in Scheme 23. As shown and according to procedures in *Angew. Chem. Int. Edn.*, (1973), 12, pp 869, the betaketoester (72) is treated with fluorosulphonyl isocyante, heated to extrude $CO_2$ and iso-butene, then treated with base such as KOH to form the oxathiazolinone dioxide intermediate (73). Treatment of (73) with triphenylmethyl chloride and triethylamine in $CH_2Cl_2$ gives (74) which in turn is converted to benzyl halide (75) by treatment with N-bromosuccinimide, AIBN, in $CCl_4$ at reflux.

SCHEME 23

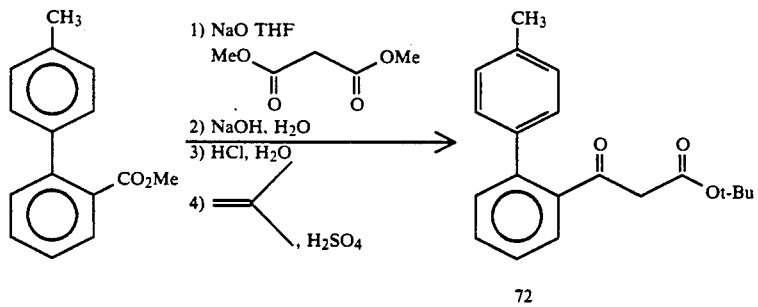

72

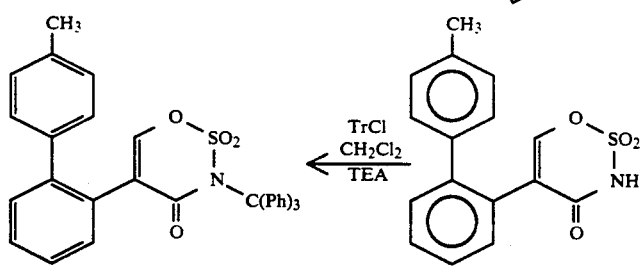

74 73

↓ NBS
AIBN
CCl₄

SCHEME 23

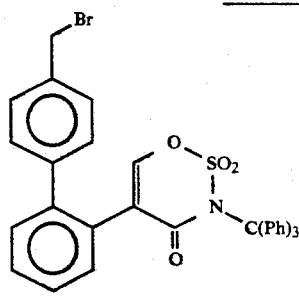

75

Compounds of Formula (I) wherein $R^1$ is oxamic acid may be prepared utilizing procedures described in J. Med. Chem., 1981, 24, pp 742–748 and as outlined in Scheme 24. The amine (35) is reacted with ethyl oxalyl chloride in the presence of a base such as pyridine or triethylamine and a solvent such as $CH_2Cl_2$ to form the intermediate oxalyl ester which is subsequently saponified with hydroxide to form oxamic acid (76).

SCHEME 24

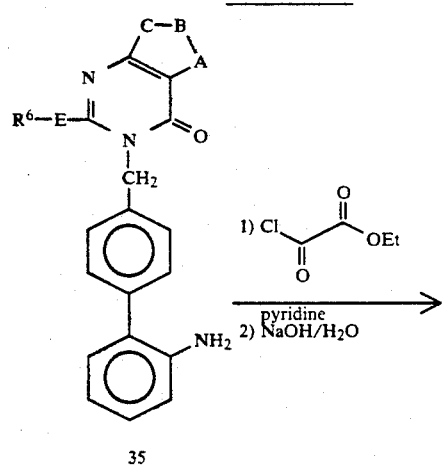

-continued
SCHEME 24

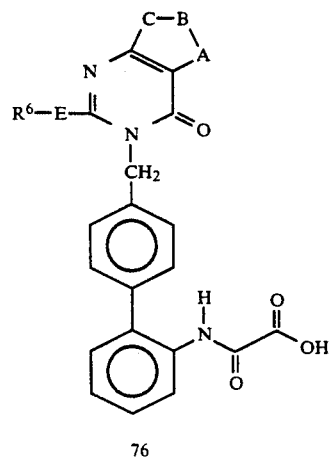

76

Compounds of Formula (I) wherein $R^1$ is $-SO_2NR^{24}OR^{24}$ may be prepared as outlined in Scheme 25. The key intermediate 79 is prepared by the reaction of an appropriate heterocyclic compound (1), preferably as an alkali metal salt, with the alkylating agent 77 (prepared from 35). The compound 81, prepared from the sulfonyl chloride 80 and O-t-butylhydroxylamine, is then reacted with 79 in the presence of a Pd(0) catalyst to give 82. Removal of the t-butyl protecting group produces the desired N-hydroxy sulfonamide 83.

SCHEME 25

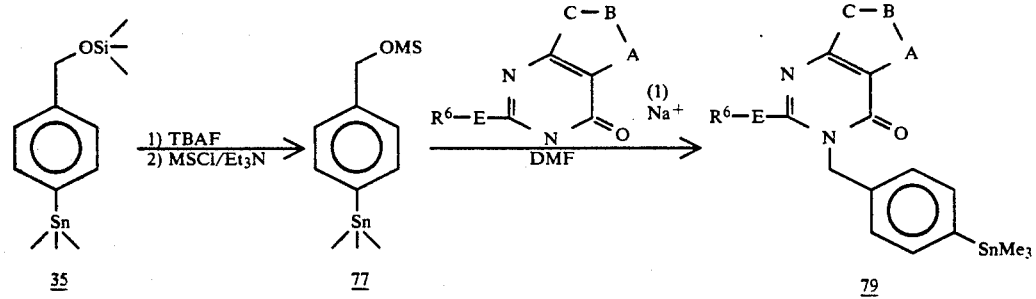

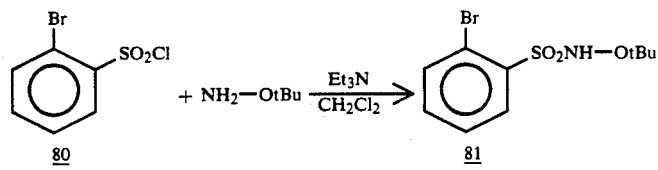

-continued
SCHEME 25

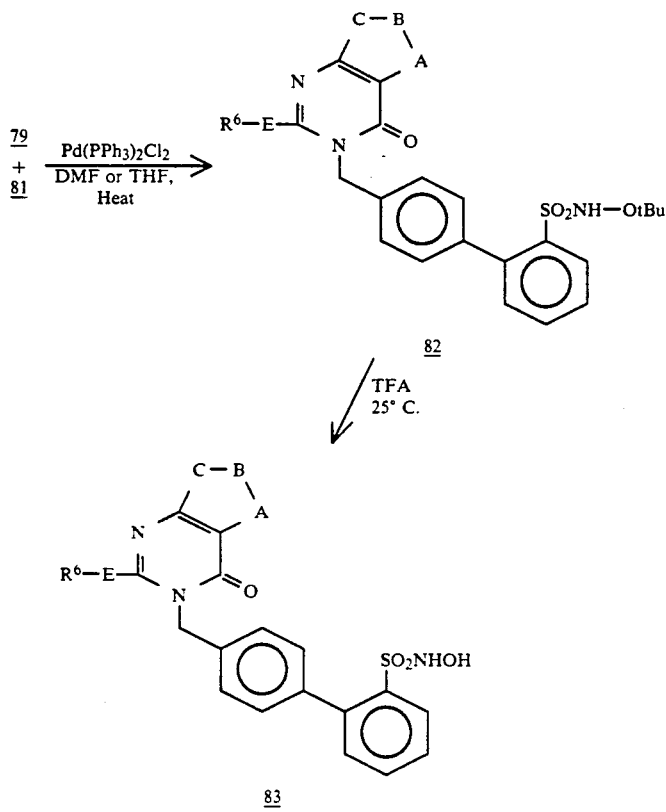

In certain cases due to the nature of the heterocycle being prepared and to the availability of starting materials, it may be advantagous to prepare some of the compounds of this invention from a suitably functionalized pyrimidinone ring and then ring closing to compounds of Formula (I). For example, appropriately functionalized 2-substituted-purine-6(1H)-one's (2) may be synthesised from 4,5-diaminopyrimidin-6(1H)-one's (84) by condensation with acids, amides, orthoesters, acid chlorides and amidines to give, following treatment with base and heat, the desired heterocycles (Scheme 26 ).[14,15,16] This conversion is known as the Taube reaction. The heterocycle may then be alkylated with (6) as shown in Scheme 2.

SCHEME 26

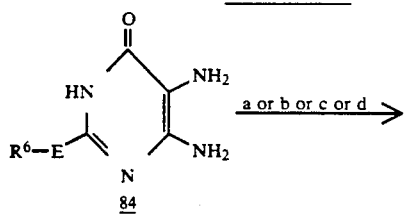

-continued
SCHEME 26

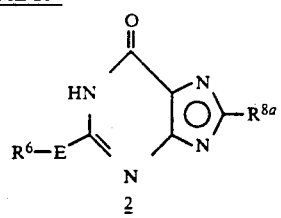

$a = R^{8a}-\overset{\overset{O}{\|}}{C}-Cl$
$b = R^{8a}-C(O(C_1-C_4\text{-alkyl}))_3$
$c = R^{8a}-\overset{\overset{O}{\|}}{C}-NH_2$
$d = R^{8a}-\overset{\overset{NH_2}{|}}{C}=NH$ An alternative method of preparing 2,8-disubstituted purin-6(1H)-ones is to condense aminomalonamidamidine (44) with ortho esters to give the heterocycle (45) (Scheme 27)[17]. This may then be selectively alkylated as shown in Scheme 2 to give compounds of Formula (I).

SCHEME 27

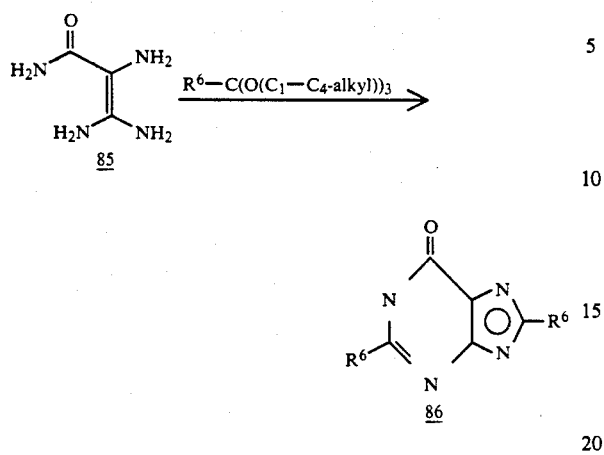

2-Substituted-furo(2,3-d)pyrimidin-4(3H)ones (87) have been prepared from acid catalysed ring closing of 5-acetonylpyrimidin-4-ones (88)[18]. (Scheme 28) The heterocycle (87) may then be alkylated with (6) as shown in Scheme 2 and deprotected as necessary to give compounds of Formula (I).

SCHEME 28

2,3,6-Trisubstituted thieno{2,3-d}pyrimidin4(3H)-ones (1) have been prepared by heating 2-acylaminothiophene-3-carboxylates (90) with phosphorous pentoxide, N,N'-dimethylcyclohexylamine and an amine hydrochloride at 180° C. (Scheme 29). [19] Deprotection of (89) would give rise to compounds of Formula I.

SCHEME 29

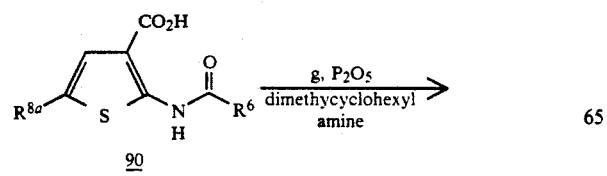

-continued
SCHEME 29

In the cases where E=O,S, a vicinally substituted amino carboxylic acid amide heterocycle (91) may be reacted with phosgene, carbonyldiimidazole, ethyl carbonate, urea, thiourea, carbon disulfide, thiophosgene and other carbonyl and thiocarbonyl equivalents to give heterocycles of structure (92) (Scheme 30). These may, under appropriate conditions, be alkylated on oxygen or sulfur to give compounds of type (93). These may, in turn, be alkylated with (6) as shown in Scheme 2 to give compounds of Formula (I).

Alternatively, (92) may be protected so as to allow conversion of the newly formed carbonyl to iminoyl chloride through the action of a chlorinating agent such as phosphoryl chloride. Reaction of the iminoyl chloride with an amine should give rise to compounds of structure (94) where E=N. These compounds may then be converted to compounds of Formula (I) by apropriate protection and alkylation with (6) as shown in Scheme 2.

SCHEME 30

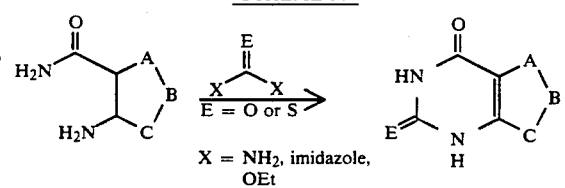

93 E = O, S
94 E = NH

SCHEME 30 -continued a. NaH, R⁶-halo, DMF
b. i) POCl₃  ii) R⁶NH₂

2-Substituted pyrrolo{3,2-d}pyrimidin-4-(3H)-ones may be prepared from enamine (95) by treatment with base to give the pyrrole (96) followed by condensation with an anhydride and treatment with base to give the pyrimidinone (97) (Scheme 31)[20]. This may, in turn, be alkylated, after appropriate protecting groups have been added, with (6) as shown in Scheme 2.

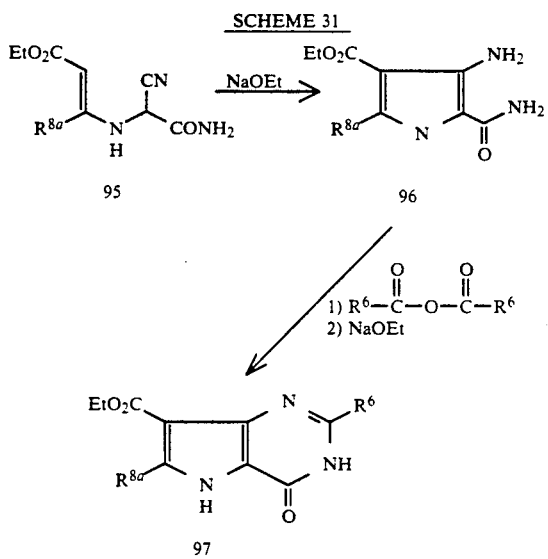

SCHEME 31

The synthesis of oxazolo{5,4-d}pyrimidin-7(6H)-ones is reported to be precluded from 2-amino-3-cyano-oxazoles via acylation and hydrolysis/cyclization with basic hydrogen peroxide due to the instability of the oxazole ring. An alternative route is available from the pyrimidinone (98) by treatment with an alkyl anhydride to give (99) (Scheme 32)[21]. This may, in turn, be alkylated with (6) as indicated in Scheme 2 to give structures of Formula (I).

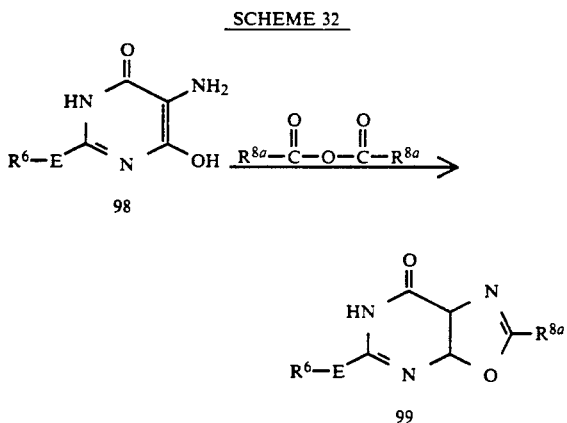

SCHEME 32

Oxazolo(4,5-d}pyrimidin-7(6H)-ones may be prepared from 2-acylamino-2-cyanoacetamides via intermediate carboxamide hydrochlorides. Thus, 2-acylamino-2-cyano acetamides (100) are converted to oxazoles (101) by treatment with acid. Condensation of the oxazoles (101) with an orthoformate gave 5-unsubstituted oxazolo{4,5-d}pyrimidin-7(6H)-ones (102) (Scheme 33).[22] Condensation with alkyl orthoformates should give rise to the 5-substituted series. Alkylation of (102) will give rise to compounds of Formula (I) as indicated in Scheme 2.

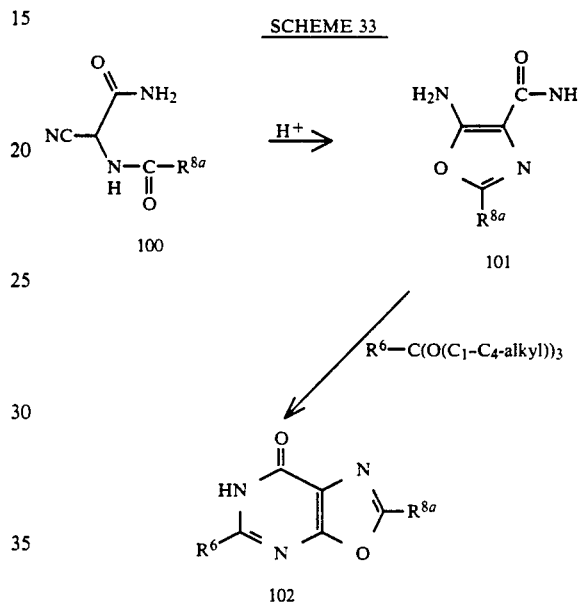

SCHEME 33

Further functionalization of compounds of Formula (I) where $R^{8a}$ or $R^{8b}$ is nitro is available through the following route (Scheme 34). The nitro group of (103) may be reduced to the amine (104) by reduction with hydrogen over palladium on carbon. The amine may then be acylated with acid chlorides to give amides under basic conditions. The acylation of the amine with chloroformates is best carried out in the presence of sodium hydride to form the anilinium anion. This anion reacts quickly with chloroformates to give the carbamates (105). The carbamate may be isolated and then deprotonated with lithium hexamethyldisilazide and alkylated to give the N,N-dialkylated carbamates (106). Alternatively this process may be carried out in one pot by first preforming the anilinium anion, acylating it and then deprotonating in situ and alkylating with $R^4$ iodide group to give (106). The amine (104) reacts slowly with isocyanates to give ureas (107). Trisubstituted ureas (108) may be prepared from the benzyl carbamate (105) ($R^{22}$=benzyl) by treatment with the magnesium salt of a secondary amine. The trisubstituted ureas may be N-alkylated by deprotonation with lithium hexamethyldisilazide and alkylation with an $R^4$ iodide to give (109). The amine may be further derivatized or converted to other groups by means of chemical procedures well known to those skilled in the art.

SCHEME 34
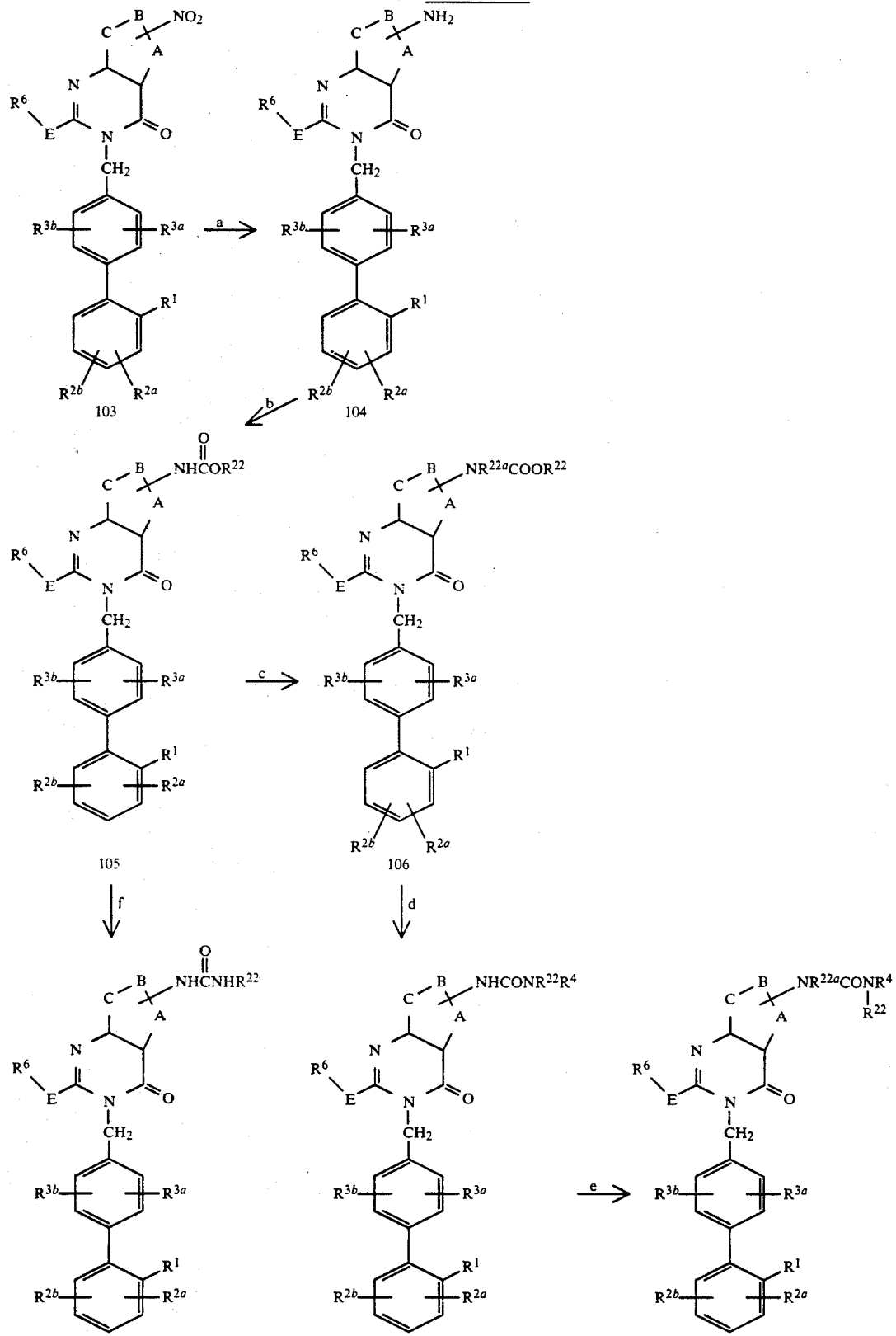
a. H$_2$, 10% Pd/C, EtAc
b. NaH, ClCOR$^{22}$, DMF

-continued
SCHEME 34 c. LiN(TMS)$_2$, R$^{22a}$I
d. MeMgBr, R$^4$NHR$^{22}$, THF, reflux
e. LiN(TMS)$_2$, R$^{22a}$I, DMF
f. R$^{22}$NCO, CH$_2$Cl$_2$ It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I. For example, R$^1$ as carboxyl is often protected as its t-butyl ester which in the last step is removed by treatment with trifluoroacetic acid.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H$_2$SO$_4$, H$_3$PO$_4$, methane-sulfonic, toluene-sulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. In order to identify AII antagonists and determine their efficacy in vitro, the following two ligand-receptor binding assays were established.

Receptor binding assay using rabbit aortae membrane preparation:

Three frozen rabbit aortae (obtained from Pel-Freeze Biologicals) are suspended in 5 mM Tris-0.25M Sucrose, pH 7.4 buffer (50 ml) homogenized, and then centrifuged. The mixture is filtered through a cheesecloth and the supernatant is centrifuged for 30 minutes at 20,000 rpm at 4° C. The pellet thus obtained is resuspended in 30 ml of 50 mM Tris-5 mM MgCl$_2$ buffer containing 0.2% Bovine Serum Albumin and 0.2 mg/ml Bacitration and the suspension is used for 100 assay tubes. Samples tested for screening are done in duplicate. To the membrane preparation (0.25 ml) there is added $^{125}$I-Sar$^1$Ile$^8$-angiotensin II [obtained from New England Nuclear] (10 ul; 20,000 cpm) with or without the test sample and the mixture is incubated at 37° C. for 90 minutes. The mixture is then diluted with ice-cold 50 mM Tris-0.9% NaCl, pH 7.4 (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration (IC$_{50}$) of potential AII antagonist which gives 50% displacement of the total specifically bound $^{125}$I-Sar$^1$Ile$^8$-angiotensin II is presented as a measure of the efficacy of such compounds as AII antagonists.

Receptor assay using Bovine adrenal cortex preparation

Bovine adrenal cortex is selected as the source of AII receptor. Weighed tissue (0.1 g is needed for 100 assay tubes) is suspended in Tris.HCl (50 mM), pH 7.7 buffer and homogenized. The homogenate is centrifuged at 20,000 rpm for 15 minutes. Supernatant is discarded and pellets resuspended in buffer [Na$_2$HPO$_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there is added 3H-angiotensin II (50 mM) (10 ul) with or without the test sample and the mixture is incubated at 37° C. for 1 hour. The mixture is then diluted with Tris buffer (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration (IC$_{50}$) of a potential AII antagonist which gives 50% displacement of the total specifically bound $^3$H-angiotensin II is presented as a measure of the efficacy of such compounds as AII antagonists.

Receptor assay using rat brain membrane preparation

Membranes from rat brain (thalamus, hypothalamus and midbrain) are prepared by homogenization in 50 mM Tris HCl (pH 7.4), and centrifuged at 50,000$\times$ g. The resulting pellets are washed twice in 100 mM NaCl, 5 mM Na$_2$.EDTA, 10 mM Na$_2$HPO$_4$ (pH 7.4) and 0.1 mM PMSF by resuspension and centrifugation. For binding assays, the pellets are resuspended in 160 volumes of binding assay buffer (100 mM NaCl, 10 mM Na$_2$HPO$_4$, 5 mM Na$_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 $\mu$l of solvent (for total binding), Sar$^1$,Ile$^8$-angiotensin II (1 $\mu$M) (for nonspecific binding) or test compounds (for displacement) and 10 $\mu$l of [$^{125}$I]Sar$^1$-,Ile$^8$-angiotensin II (23–46 pM) are added to duplicate tubes. The receptor membrane preparation (500 $\mu$l) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters is counted using a gamma counter.

Using the methodology described above, representative compounds of this invention could be evaluated and an IC$_{50}$<50 $\mu$M determined, thereby demonstrating and confirming the utility of the compounds of the invention as effective A II antagonists.

The antihypertensive effects of the compounds described in the present invention may be evaluated using the methodology described below:

Male Charles River Sprague-Dawley rats (300-375 gm) are anesthetized with methohexital (Brevital; 50 mg/kg i.p.) and the trachea is cannulated with PE 205 tubing. A stainless steel pithing rod (1.5 mm thick, 150 mm long) is inserted into the orbit of the right eye and down the spinal column. The rats are immediately placed on a Harvard Rodent Ventilator (rate—60 strokes per minute, volumn—1.1 cc per 100 grams body weight). The right carotid artery is ligated, both left and right vagal nerves are cut, and the left carotid artery is cannulated with PE 50 tubing for drug administration, and body temperature is maintained at 37° C. by a thermostatically controlled heating pad which received input from a rectal temperature probe. Atropine (1 mg/kg i.v.) is then administered, and 15 minutes later propranolol (1 mg/kg i.v.). Thirty minutes later antagonists of formula I are administered intravenously or orally. Angiotensin II is then typically given at 5, 10, 15, 30, 45 and 60 minute intervals and every half-hour thereafter for as long as the test compound showed activity. The change in the mean arterial blood pressure is recorded for each angiotensin II challenge and the precent inhibition of the angiotensin II response is calculated.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 5 to 150 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthizide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, veropamil and the like, as well as admixtures and combinations thereof.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptyl-physostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, penut oil, cottonseed oil, etc., or a synthetic fatty vehicle like ethyl oleate or the like. Buffers, preservatives, antioxidants and the like can be incorporated as required.

The following examples further illustrate the preparation of the compounds of Formula I and their incorporation into pharmaceutical compositions and, as such, are not to be considered or construed as limiting the invention recited in the appended claims.

All $^1$H-NMR spectra were recorded on a Varian XL-400 Fourier transform spectrometer unless otherwise noted. Chemical shifts are reported as (parts per million) downfield from tetramethyl silane. Mass spectra were obtained from the Merck and Co. mass spectral facility in Rahway N.J. Analytical TLC was conducted on E. M. Merck precoated silica plates (0.25 mm in glass, Kieselgel 60 $F_{254}$) with UV visualization. All chromatography was conducted on E. M. Merck silica gel. All reactions were carried out under an atmosphere of dry nitrogen under standard conditions for those skilled in the art.

EXAMPLE 1

2-n-Butyl-5-methyl-thieno{2,3-d}pyrimidin-4(3H)-one

To a solution of 3.7 g (0.2 mol) of ethyl 2-amino-4-methylthiophene-3-carboxylate in 30 ml dry dioxane was added 1.82 g (0.022 mol) of valeronitrile. The solution was treated with dry HCl gas over a period of 5 hours. The mixture was poured into 200 ml of ice water and made basic with 10% NH$_4$OH. The resulting solids were collected by filtration. A solution of the residue in MeOH was allowed to stand over 3 days and gave rise to a mass of crystals that were shown to be starting material. The filtrate was concentrated in vacuo and the residue was triturated with 20% EtOAc/hexanes. A white precipitate formed that was removed by filtration to give the desired heterocycle. $^1$H-NMR (CDCl$_3$-200 MHz): 0.97 (t, 3H, J=7.3 Hz), 1.49 (m, 2H), 1.70–1.91 (m, 3H), 2.58 (s, 3H), 2.76 (3 line m, 2H, J=8.2 Hz), 6.77 (bs, 1H).

EXAMPLE 2

2-n-Butyl-thieno{3,2-d}pyrimidin-4(3H)-one

To a solution of 3.14 g (0.02 mol) of methyl 3-aminothiophene-2-carboxylate in 30 ml of dioxane was added 1.83 g (0.022 mol) of valeronitrile. Dry HCl was added over a period of 5 hours and the reaction mixture was then heated to 70° C. for 3 hours. The mixture was allowed to stand overnight at room temperature. The reaction mixture was diluted with 200 ml of ice water, made basic by addition of NH$_4$OH and after standing for 30 minutes was filtered, and the filtrate concentrated in vacuo. The residue was purified by flash chromatography eluting with 50% EtOAc/hexanes after applying a suspension of the product in CH$_2$Cl$_2$ to the column.

$^1$H-NMR (CDCl$_3$): 0.96 (t, 3H, J=7.4 Hz), 1.44 (m, 2H), 1.62 (bs, 1H), 1.82 (m, 2H), 2.79 (3 line m, 2H, J=7.8 Hz), 7.33 (d, 1H, J=5.3 Hz), 7.81 (d, 1H, J=5.3 Hz).

EXAMPLE 3

2-Butyl-4,5,6,7-tetrahydrobenzo[b]thieno{2,3-d}pyrimidin-4(3H)-one

To a solution of 5 g (0.022 mol) of ethyl 2-amino-4,5,6,7-tetrahydrobenzothiophene-3-carboxylate and 2.6 ml (0.024 mol) of valeronitrile in 75 ml of dry dioxane was added HCl gas via a gas dispersion tube. A precipitate formed that gradually redissolved. After 5.5 hours of gas addition, the solution was heated to 70° C. for 3 hours. The reaction mixture was cooled to room temperature and stirred overnight. The mixture was poured into 300 ml of ice water and the solid residue was removed by filtration. The residue was recrystalized from MeOH to give colorless crystals of the desired product. $^1$H-NMR (CDCl$_3$): 0.93 (t, 3H, J=7.4 Hz), 1.41 (m, 2H), 1.83 (m, 6H), 2.75 (M, 4H), 2.98 (3 line m, 2H, J=5.81 Hz), 12.38 (bs, 1H).

EXAMPLE 4

GENERAL METHOD FOR ALKYLATING HETEROCYCLE WITH BIPHENYL BROMIDE

To a suspension of 1 mmol of NaH in 1 ml of dry DMF at 0° C. is added the pyrimidinone (1 mmol) as a solid under nitrogen gas. The solution is stirred for 30 minutes at which time a solution of 1.1 mmol of an appropriate 4'-bromomethylbiphenyl alkylating agent in 1.75 ml of dry DMF. The reaction mixture is stirred at room temperature overnight, diluted with 25 ml of EtOAc and washed with water (3×5 ml) and brine (1×10 ml) and dried over MgSO$_4$. The mixture is filtered, and the filtrate is concentrated in vacuo. The residue then is purified by flash chromatography over silica gel eluting with an appropriate mixture of EtOac/hexanes to give the product.

EXAMPLE 5

4'-Bromomethylbiphenyl-2-tert-butylsulfonamide

Step 1: 2-Bromobenzene(tert-butyl)sulfonamide

To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 h, then the mixture evaporated to dryness. Flash chromatography (silica gel, 10,15% ethyl acetate-hexane) afforded 2-bromobenzene(tert-butyl)sulfonamide as a white solid; $^1$H NMR (300 MHz, CDCl$_3$) δ 8.18 (d, J=8.5 Hz, 1H), 7.73 (d, J=8.5 Hz, 1H), 7.50–7.35 (m, 2H), 5.11 (s, 1H), 1.20 (s, 9H).

Step 2: p-Tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 h then saturated ammonium chloride solution (10 ml) was added followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (39°–40° C., 0.1 mm Hg) which was further purified by flash chromatography (silica gel, hexane) to give p-tolyltrimethyltin as a colorless liquid; $^1$H NMR (300 MHz, CDCl$_3$) δ 7.40 (d, J=7.7 Hz, 2H), 7.19 (d, J=7.7 Hz, 2H), 2.34 (s, 3H), 0.30 (s, 9H).

Step 3: 4'-Methylbiphenyl-2-tert-butylsulfonamide

2-Bromobenzene(tert-butyl)sulfonamide (1.00 g, 3.92 mmol), p-tolyl-trimethyltin (1.95 g, 6.67 mmol), bis(triphenylphosphine)palladium(II) chloride (Aldrich) (165 mg, 0.235 mmol) and dimethylformamide (25 ml) were heated with stirring under nitrogen at 90° C. for 5 h. The black suspension was cooled to room temperature, then filtered through a pad of celite which was washed with tetrahydrofuran. The colorless filtrate was evaporated to dryness then chromatographed (silica gel, 8,10% ethyl acetate-hexane) to give 4'-methylbiphenyl-2-tert-butylsulfonamide as a white solid; $^1$H NMR (300 MHz, CDCl$_3$) δ 8.16 (d, J=7.9 Hz, 1H), 7.60–7.37 (m, 4H), 7.36–7.24 (m, 3H), 3.57 (s, 1H), 2.42 (s, 3H), 0.99 (s, 9H).

Step 4: 4'-Bromomethylbiphenyl-2-tert-butylsulfonamide

N-Bromosuccinimide (0.387 g, 2.17 mmol), a,a'-azoisobutyronitrile (catalytic), 4'-methylbiphenyl-2-tert-butylsulfonamide (0.55 g, 1.81 mmol) and carbon tetrachloride (50 ml) were heated with stirring at reflux for 3 h. After cooling to room temperature the mixture was filtered and the filtrate evaporated to dryness. Flash chromatography (silica gel, 10,20% ethyl acetate-hexane) afforded 4'-bromomethylbiphenyl-2-tert-butylsulfonamide (77% pure (the remainder of the material was 4'-dibromomethylbiphenyl-2-tert-butylsulfonamide)) as a white solid; $^1$H NMR (300 MHz, CDCl$_3$) δ 8.17 (dd, J=7.5, 1.6 Hz, 1H), 7.68–7.45 (m, 6H), 7.31 (dd, J=7.5, 1.6 Hz, 1H), 4.55 (s, 2H), 3.52 (s, 1H), 1.00 (s, 9H).

EXAMPLE 6

2-Butyl-3-(2'-(aminosulfonyl-biphen-4-yl)methyl)-thieno{3,2-d}pyrimidin-4-one Step 1: 2-Butyl-3-(2'-(tert-butylamino-sulfonyl biphen-4-yl)-methyl)-thieno{3,2-d}pyrimidin-4-one 2-Butyl-thieno{3,2-d}pyrimidin-4-one, obtained from Example 2, is added to a stirred suspension of sodium hydride in dimethylformamide at room temperature under nitrogen. After stirring for 45 min at room temperature, a solution of 4'-(bromomethyl)-biphenyl-2-tert-butylsulfonamide in dimethylformamide is added, and the resulting mixture is stirred at room temperature overnight. After removal of the solvent in vacuo, the crude product obtained is purified by flash chromatography (silica gel) to afford the titled compound.

Step 2: 2-Butyl-3-(2'-(aminosulfonyl-biphen-4-yl)methyl)-thieno{3,2-d}pyrimidin-4-one A solution of 2-butyl-3-(2'-(tert-butylaminosulfonyl-biphen-4-yl)-methyl)-thieno{3,2-d}-pyrimidin-4-one and anisole in trifluoroacetic acid is stirred under nitrogen at room temperature for 8 h, and then the solvent is removed in vacuo. The crude product is purified by flash chromatography (silica gel) to afford the titled compound.

EXAMPLE 7

2-Butyl-3-(2'-((isopropylsulfonylamino)sulfonyl-biphen-4-yl)methyl)-thieno{3,2-d}pyrimidin-4-one To a stirred suspension of NaH in dry DMF under nitrogen at room temperature is added 2-butyl-3-(2'-(aminosulfonyl-biphen-4-yl)methyl)-thieno{3,2-d}pyrimidin-4-one. After stirring for 30 minutes at room temperature, isopropylsulfonylchloride is added and stirring continued at room temperature overnight. The reaction mixture is poured into ice water, acidified with 5% citric acid solution and extracted with chloroform. The organic phase is washed with water and brine, and then dried over MgSO$_4$. The crude product obtained after workup is purified by flash-chromatography (silica gel) to give the desired product.

EXAMPLE 8

2-Butyl-3-(2'-((dibenzylphosphonylamino)sulfonyl-biphen-4-yl)methyl)-thieno{3,2-d}pyrimidin-4-one To a stirred solution of 2-butyl-3-(2'-(aminosulfonyl-biphen-4-yl)methyl)-thieno{3,2-d}pyrimidin-4-one in dry THF is added n-BuLi at 0° C. After stirring for 15 minutes at that temperature, a solution of dibenzylphosphorylchloride in THF is added and stirring continued at room temperature overnight. The reaction mixture is concentrated under reduced pressure, and the residue is treated with 5% aqueous citric acid and extracted with methylene chloride. The organic phase is washed with water and brine, and then dried over MgSO$_4$. The crude product obtained after removal of the solvent is purified on silica-gel by flash-chromatography to give the titled product.

EXAMPLE 9

4'-Bromomethylbiphenyl-2-(O-tert-butyl)-N-hydroxysulfonamide

Step 1: Preparation of 2-bromobenzene(O-tert-butyl)-N-hydroxysulfonamide

To a stirred solution of 2-bromobenzenesulfonyl chloride (Lancaster Synthesis) (1.0 g, 4.0 mmol) in chloroform (10 ml) under nitrogen at 0° C. was added O-tert-butylhydroxylamine hydrochloride (Fluka) (0.6 g, 4.77 mmol) in three portions. The solution was stirred at room temperature for 18 h and then diluted with methylene chloride (20 ml). The organic phase was washed successively with 5% citric acid, water and then dried over MgSO4. Removal of the solvent in vacuo gave the crude product as white solid, which was then purified by flash chromatography (silica gel, 10% ethyl acetate-hexane) to afford 2-bromobenzene(O-tert-butyl)N-hydroxysulfonamide (1.12 g, 89%) as a white solid;

1H NMR (300 MHz, CDCl3) δ 8.15 (dd, J=7.5, 2.1 Hz, 1H), 7.75 (d, J=7.6, 1.8 Hz, 1H), 7.55–7.35 (m, 3H), 5.11 (s, 1H), 1.21 (s, 9H). FAB-MS: 309 (M+H).

Step 2: 4'-Methylbiphenyl-2-(O-tert-butyl)-N-hydroxysulfonamide

A solution of 2-bromobenzene(O-tert-butyl)-N-hydroxysulfonamide (0.31 g, 1.0 mmol), p-tolyltrimethyltin (0.3 g, 1.18 mmol) and bis(triphenylphosphine)palladium(II) chloride (Aldrich) (0.036 g) in dry dimethylformamide (6 ml) was stirred under nitrogen at 90° C. for 6 h. The black suspension was cooled to room temperature, then filtered through a pad of celite which was washed with tetrahydrofuran. The colorless filtrate was evaporated to dryness then purified by flash chromatography (silica gel, 8% ethyl acetate-hexane) to give the titled compound as a semi-solid mass. 1H NMR (300 MHz, CDCl3) δ 8.15 (d, J=7.8, 1.6 Hz, 1H), 7.67–7.50 (m, 2H), 7.36–7.24 (m, 5H), 5.78 (s, 1H), 2.42 (s, 3H), 1.08 (s, 9H). FAB-MS: 320 (M+H).

Step 3: 4'-Bromomethylbiphenyl-2-(O-tert-butyl)-N-hydroxysulfonamide

A mixture of N-Bromosuccinimide (0.14 g, 0.78 mmol), a,a'-azoisobutyronitrile (10 mg) and 4'-methylbiphenyl-2-(O-tert-butyl)-N-hydroxy sulfonamide (0.25 g, 0.78 mmol) in carbon tetrachloride (10 ml) was refluxed for 7 h. After cooling to room temperature the mixture was filtered and the filtrate evaporated to dryness. Flash chromatography (silica gel, 10% ethyl acetate-hexane) afforded 4'-methylbiphenyl-2-(O-tert-butyl)-N-hydroxy sulfonamide as a white solid. 1H NMR (300 MHz, CDCl3) δ 8.15 (d, J=7.8 Hz, 1H), 7.70–7.30 (m, 7H), 5.72 (s, 1H), 4.55 (s, 2H), 1.08 (s, 9H). FAB-MS: 398, 400 (M+H).

EXAMPLE 10

2-Butyl-3-(2'-((N-hydroxyamino)sulfonyl-biphen-4-yl)methyl)-thieno{3,2-d}pyrimidin-4-one Step 1: 2-Butyl-3-(2'-((O-tert-butyl-N-hydroxyamino)sulfonyl-biphen-4-yl)methyl)thieno{3,2-d}pyrimidin-4-one 2-Butyl-thieno{3,2-d}pyrimidin-4-one is added to a stirred suspension of sodium hydride in dimethylformamide at room temperature under nitrogen. After stirring for 45 min at room temperature, a solution of 4'-bromomethylbiphenyl2-(O-tert-butyl)-N-hydroxy-sulfonamide in dimethylformamide is added dropwise, and the resulting solution is stirred at room temperature overnight. The solvent is removed in vacuo, and the crude product obtained is purified by flash chromatography (silica gel) to afford the titled compound.

Step 2: 2-Butyl-3-(2'-((N-hydroxyamino)sulfonyl-biphen-4-yl)methyl)-thieno{3,2-d}pyrimidin-4-one A solution of 2-butyl-3-(2'-((O-tert-butyl-N-hydroxyamino)sulfonyl-biphen-4-yl)methyl)-thieno{3,2-d}pyrimidin-4-one and anisole in trifluoroacetic acid is stirred under nitrogen at room temperature for 24 h, and then the solvent is removed in vacuo. The residue is triturated with dry ether, and the resulting solid is collected by filteration. The solid is finally crystallized from an appropriate solvent to give the titled product.

EXAMPLES 11 TO 20

The compounds of the Formula (VII) exemplified in Table F are prepared from the appropriate substituted starting materials utilizing the general procedures outlined in the examples hereinabove and the noted schemes.

TABLE F

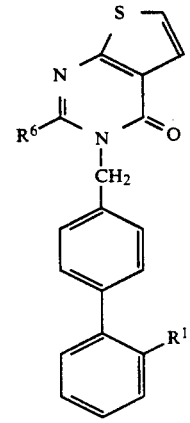
(VII)

| Example # | R1 | R6 | Scheme |
|---|---|---|---|
| 11 | —SO2NHSO2Me | Bu | 8 |
| 12 | —SO2NHSO2iPr | Pr | 8 |
| 13 | ![structure] | Bu | 16,17 |
| 14 | ![structure N—N—Ph] | Bu | 18–20 |
| 15 | —NH—C(O)—COH | Pr | 25 |
| 16 | —SO2NHSO2iPr | Bu | 8 |
| 17 | —SO2NHPOCH2Ph (OCH2Ph) | Pr | 13 |
| 18 | ![structure] | Pr | 21 |
| 19 | ![structure NHSO2Ph] | Pr | 11 |

TABLE F-continued (VII)

| Example # | R¹ | R⁶ | Scheme |
|---|---|---|---|
| 20 | (N-O-S(=O)₂-N=) | Bu | 15 |

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 2-Butyl-3-(2'-((isopropyl-sulfonylamino)sulfonyl-biphen-4-yl)methyl)-thieno{3,2-d}pyrimidin-4-one | 50 |
| Lactose | 149 |
| Magnesium stearate | 1 |
| Capsule (size No. 1) | 200 |

2-Butyl-3-(2'-((isopropyl-sulfonylamino)-sulfonyl-biphen-4-yl)methyl)-thieno{3,2-d}pyrimidin-4-one can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-butyl-3-(2'-((isopropyl-sulfonylamino)-sulfonyl-biphen-4-yl)methyl)-thieno{3,2-d}pyrimidin-4-one (25 mg), pregelatinized starch USP (82 mg), microcrystaline cellulose (82 mg) and magnesium stearate (1 mg).

C: Combination Tablet

A typical combination tablet would contain, for example, a diuretic such as hydrochlorothiazide and consist of 2-butyl-3-(2'-((isopropyl-sulfonylamino)-sulfonyl-biphen-4-yl)methyl)-thieno{3,2-d}pyrimidin-4-one (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain 2-butyl-3-(2'-((isopropyl-sulfonylamino)-sulfonyl-biphen-4-yl)methyl-thieno{3,2-d}pyrimidin-4-one (1–25 mg), butylated hydroxyanisole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain 2-butyl-3-(2'-((isopropyl-sulfonylamino)-sulfonyl-biphen-4-yl)methyl)-thieno{3,2-d}pyrimidin-4-one (5.42 mg), sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of the Formula (I)

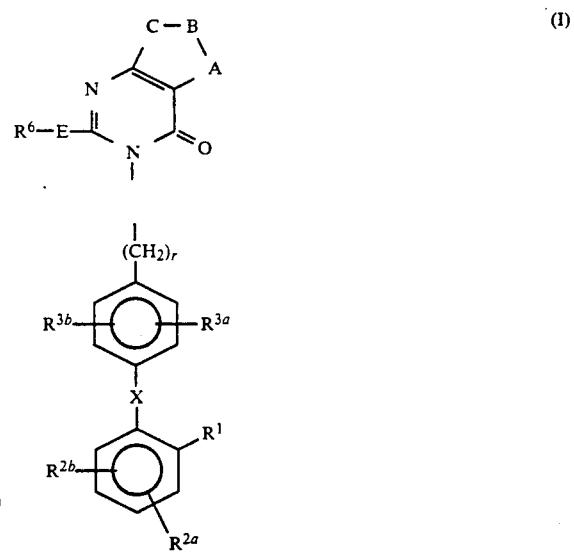

wherein:

A—B—C together with the pyrimidinone to which it is attached form a member selected from the group:

(a) 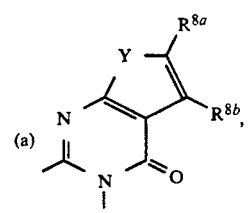

-continued
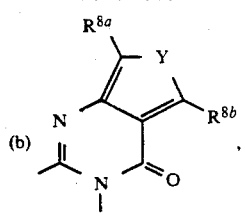
(b)
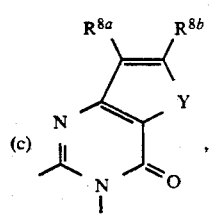
(c)
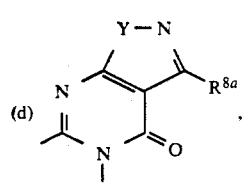
(d)
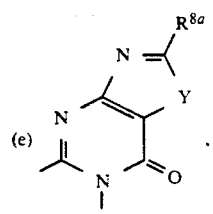
(e)
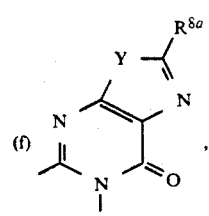
(f)
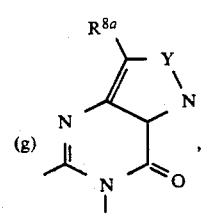
(g)
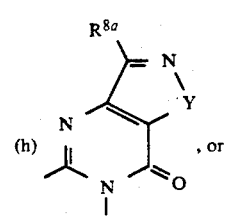
(h) , or
-continued
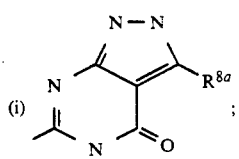
(i) ;
Y is O, or S;
R¹ is
(a) —SO₂N(R²⁴)—OR²⁴,
(b) —SO₂NHSO₂R²³,
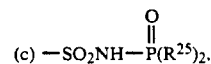
(c)
(d)
(e) —SO₂NHCN,
(f) —SO₂NHCO₂R²³,
(h) —NHSO₂NHSO₂R²³,
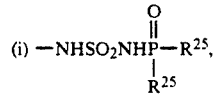
(i)
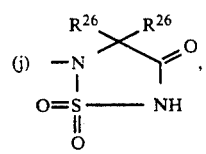
(j)
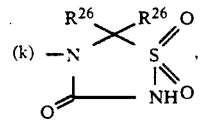
(k)
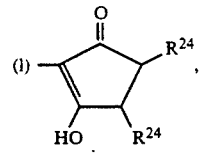
(l)
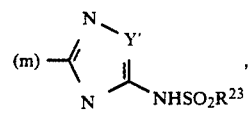
(m)
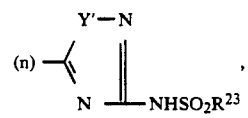
(n)
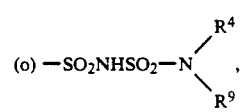
(o)

-continued (p) 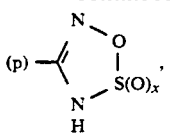, (q) 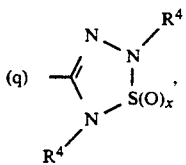, (r) 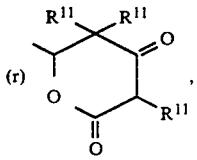, (s) 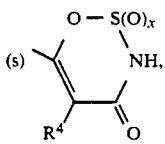, (t) 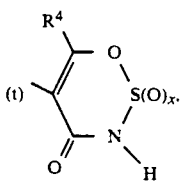.

(u) 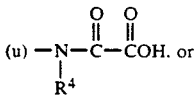 or (v) —NHSO$_2$R$^{23}$;

wherein
Y$^1$ is O or S;
R$^{2a}$ and R$^{2b}$ are each independently
(a) H,
(b) Cl, Br, I, or F,
(c) NO$_2$,
(d) NH$_2$,
(e) C$_1$-C$_4$-alkylamino,
(f) di(C$_1$-C$_4$-alkyl)amino,
(g) SO$_2$NHR$^9$,
(h) CF$_3$,
(i) C$_1$-C$_6$-alkyl,
(j) C$_1$-C$_6$-alkoxy,
(k) C$_1$-C$_6$-alkyl-S-,
(l) C$_2$-C$_6$-alkenyl,
(m) C$_2$-C$_6$-alkynyl,
(n) aryl,
(o) aryl(C$_1$-C$_4$-alkyl), or
(p) C$_3$-C$_7$-cycloalkyl;
R$^{3a}$ is
(a) H,
(b) Cl, Br, I, or F,
(c) C$_1$-C$_6$-alkyl,
(d) C$_1$-C$_6$-alkoxy, or
(e) C$_1$-C$_6$-alkoxyalkyl;
R$^{3b}$ is (a) H,
(b) Cl, Br, I, or F,
(c) NO$_2$,
(d) C$_1$-C$_6$-alkyl,
(e) C$_1$-C$_6$-acyloxy,
(f) C$_3$-C$_7$-cycloalkyl,
(g) C$_1$-C$_6$-alkoxy,
(h) —NHSO$_2$R$^4$,
(i) hydroxy(C$_1$-C$_4$-alkyl),
(j) aryl(C$_1$-C$_4$-alkyl),
(k) C$_1$-C$_4$-alkylthio,
(l) C$_1$-C$_4$-alkyl sulfinyl,
(m) C$_1$-C$_4$-alkyl sulfonyl,
(n) NH$_2$,
(o) C$_1$-C$_4$-alkylamino,
(p) di(C$_1$-C$_4$-alkyl)amino,
(q) fluoro-C$_1$-C$_4$-alkyl-,
(r) —SO$_2$—NHR$^9$,
(s) aryl,
(t) furyl,
(u) CF$_3$,
(v) C$_2$-C$_6$-alkenyl, or
(w) C$_2$-C$_6$-alkynyl;
wherein aryl is phenyl or naphthyl or substituted phenyl or naphthyl with one or two substituents selected from the group consisting of Cl, Br, I, F, N(R$^4$)$_2$, CO$_2$R$^4$, C$_1$-C$_4$-alkyl, C$_1$-C$_4$-alkoxy, NO$_2$, CF$_3$, C$_1$-C$_4$-alkylthio, —SO$_2$NR$^9$R$^{10}$, C$_3$-C$_7$-cycloalkyl, C$_3$-C$_{10}$-alkenyl, or OH;
R$^4$ is H, aryl as defined hereinabove, C$_1$-C$_6$ alkyl, or substituted C$_1$-C$_6$ alkyl with an aryl or heteroaryl substituent, wherein heteroaryl is an unsubstituted, monosubstituted or disubstituted heteroaromatic 5 or 6 membered cyclic which contains one to three heteratoms selected from the group consisting of N, O and S, and wherein the substituents are members selected from the group consisting of —OH, —SH, C$_1$-C$_4$-alkyl, C$_1$-C$_4$-alkoxy, —CF$_3$, Cl, Br, I, F, and NO$_2$;
R$^{4a}$ is aryl, C$_1$-C$_6$ alkyl, or aryl-C$_1$-C$_6$-alkyl;

R$^5$ is H, 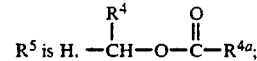;

E is a single bond, —NR$^{13}$(CH$_2$)$_s$—, —S(O)$_x$(CH$_2$)$_s$— where x is 0 to 2 and s is 0 to 5, —CH(OH)—, —O—, CO—;
R$^6$ is
(a) aryl,
(b) C$_1$-C$_6$-alkyl, C$_2$-C$_5$-alkenyl or C$_2$-C$_5$-alkynyl or substituted C$_1$-C$_6$-alkyl, C$_2$-C$_5$-alkenyl or C$_2$-C$_5$-alkynyl substituted with a substituent selected from the group consisting of aryl, C$_3$-C$_7$-cycloalkyl, Cl, Br, I, F, CF$_3$, CF$_2$CF$_3$, —NH$_2$, —NH(C$_1$-C$_4$-alkyl), —OR$^4$ —N(C$_1$-C$_4$-alkyl)$_2$, —NH—SO$_2$R$^4$, —COOR$^4$, or —SO$_2$NHR$^9$,
(c) heteroaryl as defined hereinabove,
(d) C$_3$-C$_7$-cycloalkyl,
(e) perfluoro-C$_1$-C$_4$-alkyl, or
(f) H;
R$^7$ is:
(a) H,
(b) C$_1$-C$_6$-alkyl, C$_2$-C$_6$-alkenyl or C$_2$-C$_6$-alkynyl or substituted C$_1$-C$_6$-alkyl, C$_2$-C$_6$-alkenyl or C$_2$-C$_6$-alkynyl substituted with a substituent selected from the group consisting of C$_3$-C$_7$- cycloalkyl, Cl, Br, I, F, —OH, —$NH_2$, —NH(-$C_1$-$C_4$-alkyl), —N($C_1$-$C_4$ alkyl)$_2$, —$NHSO_2R^4$, —$COOR^4$, $C_1$-$C_4$-alkoxyl, $C_1$-$C_4$-alkylthio, —$CONH_2$, —$COR^4$, or —$SO_2R^4$, —$NR^4COR^{22}$, —$NR^4CO_2R^{22}$, —$NR^4CONR^4R^{22}$, or —CO-heteroaryl,
(c) —$COR^4$,
(d) phenyl or naphthyl or substituted phenyl or naphthyl with one or two substituents wherein the substitutents are V or W,
(e) phenyl-$C_1$-$C_6$-alkyl or naphthyl-$C_1$-$C_6$-alkyl in which the phenyl or naphthyl group is unsubstituted, mono- or disubstituted with V or W,
(f) —$OR^4$,
(g) heteroaryl, or
(h) —CON($R^4$)$_2$;

V and W are independently:
(a) H,
(b) $C_1$-$C_5$-alkoxy,
(c) $C_1$-$C_5$-alkyl,
(d) hydroxy,
(e) $C_1$-$C_5$-alkyl-S(O)$_x$—,
(f) CN,
(g) $NO_2$,
(h) N($R^4$)$_2$,
(i) CON($R^4$)$_2$,
(j) $CO_2R^4$,
(k) $COR^4$,
(l) $CF_3$,
(m) Cl, Br, I, or F,
(n) hydroxy-$C_1$-$C_5$-alkyl,
(o) $C_1$-$C_5$-alkylthio,
(p) —$SO_2NR^9R^{10}$,
(q) $C_3$-$C_7$-cycloalkyl, or
(r) $C_2$-$C_{10}$-alkenyl;

$R^{8a}$ and $R^{8b}$ are independently
(a) H,
(b) $C_1$-$C_8$-alkyl, $C_2$-$C_6$-alkenyl or $C_2$-$C_6$-alkynyl or substituted $C_1$-$C_8$-alkyl, $C_2$-$C_6$-alkenyl or $C_2$-$C_6$-alkynyl with a substituent selected from the group consisting of —OH, -guanidino, $C_1$-$C_4$-alkoxy, —N($R^4$)$_2$, $COOR^4$, —CON($R^4$)$_2$, —O—$COR^4$, -aryl, -heteroaryl, —S(O)$_x$—$R^{22}$, -tetrazol-5-yl, —$CONHSO_2R^{22}$, —$SO_2NH$-heteroaryl, —$SO_2NHCOR^{22}$, —PO(O$R^4$)$_2$, —PO(O$R^4$)$R^9$, —$SO_2NH$—CN, —$NR^{10}COOR^{22}$, —(CH$_2$)$_{1-4}R^4$, Cl, Br, F, or I,
(c) —CO-aryl,
(d) —$C_3$-$C_7$-cycloalkyl,
(e) Cl, Br, I, or F,
(f) —OH,
(g) —$OR^{22}$,
(h) —$C_1$-$C_4$-perfluoroalkyl,
(i) —S(O)$_x$—$R^{22}$,
(j) —$COOR^4$,
(k) —$SO_3H$,
(l) —$NR^{22a}R^{22}$,
(m) —$NR^4COR^{22}$,
(n) —$NR^4COOR^{22}$,
(o) —$SO_2NR^4R^9$,
(p) —$NO_2$,
(q) —N($R^{22a}$)$SO_2R^{22}$,
(r) —$NR^{22a}CONR^4R^{22}$,

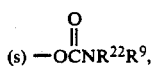
(s) —$OCNR^{22}R^9$, (t) -aryl or -heteroaryl,
(u) —$SO_2NH$-heteroaryl,
(v) —$SO_2NHCOR^{22}$,
(w) —$CONHSO_2R^{22}$,
(x) —PO(O$R^4$)$_2$,
(y) —PO(O$R^4$)$R^4$,
(z) -tetrazol-5-yl,
(aa) —CONH(tetrazol-5-yl),
(bb) —$COR^4$,
(cc) —$SO_2NHCN$,
(dd) —$NR^4SO_2NR^4R^{22}$,
(ee) —$NR^4SO_2OR^{22}$,
(ff) —$CONR^4R^{22}$,

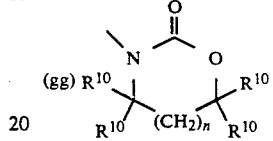

where n = 0 or 1, or

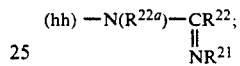

$R^9$ is H, $C_1$-$C_5$-alkyl, aryl or arylmethyl;
$R^{10}$ is H, $C_1$-$C_4$-alkyl;
$R^{11}$ is H, $C_1$-$C_6$-alkyl, $C_1$-$C_4$-alkenyl, $C_1$-$C_4$-alkoxy alkyl, or

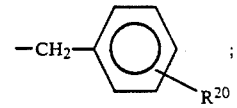

$R^{12}$ is —CN, —$NO_2$, —$CF_3$ or —$CO_2R^4$;
$R^{13}$ is H, ($C_1$-$C_4$-alkyl)CO—, $C_1$-$C_6$-alkyl, allyl, $C_3$-$C_6$-cycloalkyl, aryl or arylmethyl;
$R^{14}$ is H, $C_1$-$C_8$-alkyl, $C_1$-$C_8$-perfluoroalkyl, $C_3$-$C_6$-cycloalkyl, aryl or arylmethyl;
$R^{15}$ is H, $C_1$-$C_6$-alkyl;
$R^{16}$ is H, $C_1$-$C_6$-alkyl, $C_3$-$C_6$-cycloalkyl, aryl or arylmethyl;
$R^{17}$ is —$NR^9R^{10}$, —$OR^{10}$, —$NHCONH_2$, —$NHCSNH_2$,

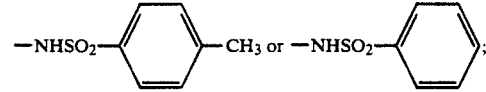

$R^{18}$ and $R^{19}$ are independently $C_1$-$C_4$-alkyl or taken together are —(CH$_2$)$_q$— where q is 2 or 3;
$R^{20}$ is H, —$NO_2$, —$NH_2$, —OH or —$OCH_3$;
$R^{21}$ is
(a) aryl,
(b) heteroaryl, or
(c) $C_1$-$C_4$-alkyl or substituted $C_1$-$C_4$-alkyl with a substituent selected from the group consisting of aryl, heteroaryl as defined above, —OH, —$NH_2$, —NH($C_1$-$C_4$-alkyl), —N($C_1$-$C_4$-alkyl)$_2$, —$CO_2R^{4a}$, Cl, Br, F, I, or —$CF_3$;
$R^{22}$ is
(a) aryl,
(b) heteroaryl, (c) $C_3$-$C_7$-cycloalkyl, (d) $C_1$-$C_6$-alkyl or substituted $C_1$-$C_6$-alkyl with a substituent selected from the group consisting of aryl, heteroaryl, —OH, —SH, $C_1$-$C_4$-alkyl, —O($C_1$-$C_4$-alkyl), —S($C_1$-$C_4$-alkyl), —$CF_3$, Cl, Br, F, I, —$NO_2$, —$CO_2H$, $CO_2$—($C_1$-$C_4$-alkyl), —$NH_2$, —NH($C_1$-$C_4$-alkyl), —N($C_1$-$C_4$-alkyl)$_2$, —$PO_3H_2$, —PO(OH)(O-$C_1$-$C_4$-alkyl), —PO(OR$^4$)R$^9$, morpholinyl or N—$C_1$-$C_4$ alkyl piperazinyl, or (e) perfluoro-$C_1$-$C_4$-alkyl;

$R^{22a}$ is (a) hydrogen, (b) aryl, (c) heteroaryl, (d) $C_3$-$C_7$-cycloalkyl, (e) $C_1$-$C_6$-alkyl or substituted $C_1$-$C_6$-alkyl with a substituent selected from the group consisting of aryl, heteroaryl, —OH, —SH, $C_1$-$C_4$-alkyl, —O($C_1$-$C_4$-alkyl), —S($C_1$-$C_4$-alkyl), —$CF_3$, Cl, Br, F, I, —$NO_2$, —$CO_2H$, $CO_2$—($C_1$-$C_4$-alkyl), —$NH_2$, —NH($C_1$-$C_4$-alkyl), —N($C_1$-$C_4$-alkyl)$_2$, —$PO_3H_2$, —PO(OH)(O—$C_1$-$C_4$-alkyl), —PO(OR$^4$)R$^9$, morpholinyl or N—($C_1$-$C_4$-alkyl)-piperazinyl, or (f) perfluoro-$C_1$-$C_4$-alkyl;

$R^{23}$ is (a) aryl, (b) heteroaryl, (c) $C_3$-$C_4$-cycloalkyl, (d) $C_1$-$C_4$-alkyl or substituted $C_1$-$C_4$ alkyl with a substituent that is a member selected from the group consisting of aryl, heteroaryl, —OH, —SH, —$C_1$-$C_4$-alkyl, —$C_3$-$C_7$-cycloalkyl, —O($C_1$-$C_4$-alkyl), —S(O)$_x$($C_1$-$C_4$-alkyl), —$CF_3$, Cl, Br, F, I, —$NO_2$, —$CO_2H$, —$CO_2$-$C_1$-$C_4$-alkyl, —$NH_2$, —NH($C_1$-$C_4$-alkyl), —NHCOR$^{4a}$, —N($C_1$-$C_4$-alkyl)$_2$, —PO(OH)(-$C_1$-$C_4$-alkyl), —PO(OH)(aryl), or —PO(OH)(O-$C_1$-$C_4$-alkyl); where x is 0 to 2, or (e) perfluoro-$C_1$-$C_4$-alkyl;

$R^{24}$ is (a) H, (b) aryl as defined above, or (c) $C_1$-$C_6$-alkyl optionally substituted with aryl, F, Cl, Br, —OH, —$NH_2$, —NH($C_1$-$C_4$-alkyl), —N($C_1$-$C_4$-alkyl)$_2$, or $CF_3$;

$R^{25}$ is (a) aryl as defined above, (b) $C_1$-$C_6$-alkyl optionally substituted with aryl, F, Cl, Br, —OH, —$NH_2$, —NH($C_1$-$C_4$-alkyl), —N($C_1$-$C_4$-alkyl)$_2$, $CF_3$, —COOR$^4$, or CN, (c) —OCH(R$^4$)—O—CO—R$^{4a}$, or (d) —OH, —O—$C_1$-$C_6$-alkyl wherein alkyl is as defined in (b);

$R^{26}$ is (a) H, (b) $C_1$-$C_6$-alkyl optionally substituted with aryl, F, Cl, Br, —OH, —$NH_2$, —NH($C_1$-$C_4$-alkyl), —N($C_1$-$C_4$-alkyl)$_2$, $CF_3$, —COOR$^4$, or CN, or (c) F, Cl, Br;

X is (a) a carbon-carbon single bond, (b) —CO—, (c) —O—, (d) —S—, (e) —N—,
    |
    R$^{13}$ (f) —CON—,
       |
       R$^{15}$ (g) —NCO—,
     |
     R$^{15}$ (h) —OCH$_2$—, (i) —CH$_2$O—

(j) —SCH$_2$—, (k) —CH$_2$S—, (l) —NHC(R$^9$)(R$^{10}$), (m) —NR$^9$SO$_2$—, (n) —SO$_2$NR$^9$—, (o) —C(R$^9$)(R$^{10}$)NH—, (p) —CH=CH—, (q) —CF=CF—, (r) —CH=CF—, (s) —CF=CH—, (t) —CH$_2$CH$_2$—, (u) —CF$_2$CF$_2$—,

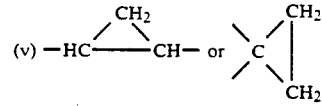

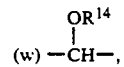

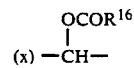

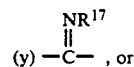

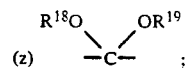

r is 1 or 2; and a pharmaceutically acceptable salt thereof.

2. A compound of claim 1 wherein:

$R^1$ is:

(a) —SO$_2$N(R$^{24}$)—OR$^{24}$, (b) —SO$_2$NHSO$_2$R$^{23}$,

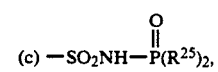

(d) —SO$_2$NHCN, (e) —SO$_2$NHCO$_2$R$^{23}$,

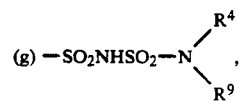

(h) —NHSO$_2$NHSO$_2$R$^{23}$,

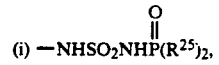

-continued (j) 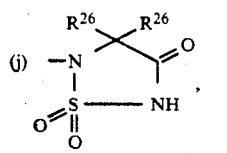

(k) 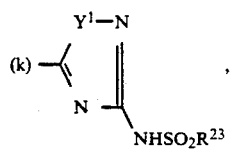

(l) 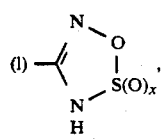

(m) 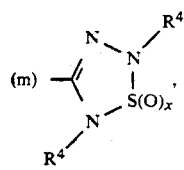

(n) 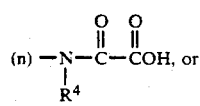

(o) —NHSO$_2$R$^{23}$;

R$^{2a}$ is H;
R$^{2b}$ is H, F, Cl, CF$_3$, C$_1$-C$_6$-alkyl, C$_2$-C$_6$-alkenyl, C$_2$-C$_6$-alkynyl, or aryl;
R$^{3a}$ is H;
R$^{3b}$ is H, F, Cl, CF$_3$, C$_1$-C$_4$-alkyl, C$_2$-C$_4$-alkenyl, C$_2$-C$_4$-alkynyl, C$_5$-C$_6$-cycloalkyl, —COOCH$_3$, —COOC$_2$H$_5$, —SO$_2$—CH$_3$, NH$_2$, —N(C$_1$-C$_4$-alkyl)$_2$ or —NH—SO$_2$CH$_3$;
E is a single bond, —O— or —S—;
R$^6$ is
  (a) C$_1$-C$_5$ alkyl or substituted C$_1$-C$_5$ alkyl with a substituent selected from the group consisting of C$_3$-C$_5$-cycloalkyl, Cl, CF$_3$, CCl$_3$, —O—CH$_3$, —OC$_2$H$_5$, —S—CH$_3$, —S—C$_2$H$_5$, phenyl, or F,
  (b) C$_2$-C$_5$-alkenyl or C$_2$-C$_5$-alkynyl, or,
  (c) C$_3$-C$_5$-cycloalkyl;
R$^7$ is
  (a) H;
  (b) C$_1$-C$_6$-alkyl or substituted C$_1$-C$_6$-alkyl with a —OH, —N(R$^4$)$_2$, —NR$^4$COR$^{22}$—NR$^4$CO$_2$R$^{22}$, or —NR$^4$CONR$^4$R$^{22}$ substituent; or
  (c) phenyl or naphthyl or substituted phenyl or naphthyl with a Cl, —F, —O(C$_1$-C$_4$-alkyl), —CO$_2$R$^4$, or —SO$_2$R$^4$ substituent;
R$^{8a}$ and R$^{8b}$ are independently
  (a) H,
  (b) C$_1$-C$_8$-alkyl or substituted C$_1$-C$_8$-alkyl with COOR, OCOR$^{4a}$, OH, aryl, or —(CH$_2$)$_{1-4}$R$^4$ substituent,
  (c) OR$^{22}$,
  (d) —OH,
  (e) —NO$_2$,
  (f) —N(R$^{22a}$)COR$^{22}$,
  (g) —CONR$^4$R$^{22}$,
  (h) —N(R$^{22a}$)CO$_2$R$^{22}$,
  (i) —NR$^4$R$^{22}$,
  (j) Cl, F, or Br,
  (k) —CF$_3$,
  (l) —CO$_2$R$^{4a}$,
  (m) —CO—aryl,
  (n) —S(O)$_x$—R$^{22}$,
  (o) —SO$_2$—NR$^4$R$^9$,
  (p) —N(R$^{22a}$)SO$_2$R$^{22}$,
  (q) aryl,
  (r) —NR$^{22a}$CONR$^4$R$^{22}$, or
  (s) —N(R$^{22a}$)SO$_2$N(R$^4$)R$^{22}$;
X is a single bond; and
r is one.

3. A compound of claim 2 wherein:
A—B—C together with the pyrimidinone to which it is attached form a member selected from the group:

(a) 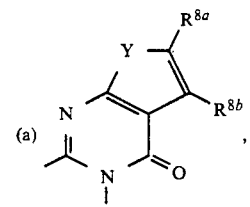

(b) 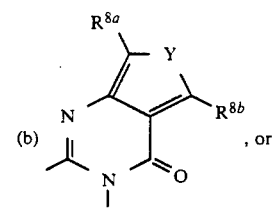, or (c) 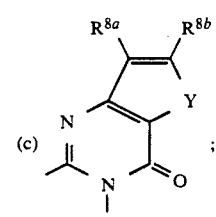;

Y is O, or S;
E is a single bond;
R$^{2b}$ and R$^{3b}$ are H;
R$^6$ is C$_1$-C$_4$-alkyl, C$_2$-C$_5$-alkenyl, cyclopropyl, —CH$_2$CH$_2$CF$_3$, —CH$_2$CH$_2$CH$_2$CF$_3$ or cyclopropylmethyl; and
R$^{8a}$ and R$^{8b}$ are each independently H, —C$_1$-C$_4$ alkyl, —NO$_2$, —NR$^4$R$^{22}$, —OCH$_3$, —NR$^{22a}$COOR$^{22}$, —Cl, CH$_2$COOR$^{4a}$, -S(O)$_x$—R$^{22}$, —NR$^{22a}$CONR$^4$R$^{22}$, —CH$_2$OCO(C$_1$-C$_4$-alkyl), —NR$^{22a}$COR$^{22}$, —CO$_2$R$^{4a}$, —F, —CH$_2$Ph, or —CONR$^4$R$^{22}$.

4. A compound of claim 2 wherein:
A—B—C together with the pyrimidinone to which it is attached form a member selected from the groups:

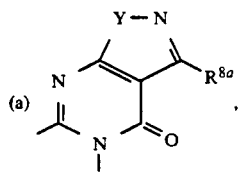
(a),

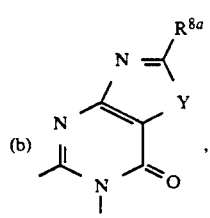
(b),

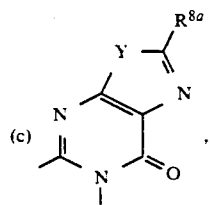
(c),

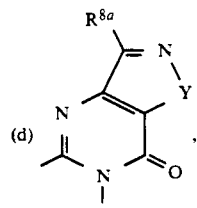
(d),

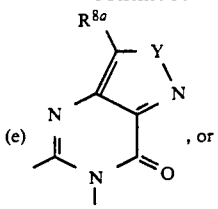
(e), or

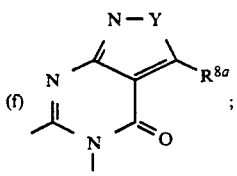
(f);

Y is O, or S;
$R^{2a}$, $R^{2b}$, $R^{3a}$ and $R^{3b}$ independently are:
(a) hydrogen,
(b) $C_1$-$C_6$-alkyl,
(c) $C_2$-$C_6$-alkenyl,
(d) $C_2$-$C_6$-alkynyl,
(e) Cl,
(f) F,
(g) $NO_2$, or
(h) $CF_3$;
$R^6$ is $C_1$-$C_4$-alkyl, $C_2$-$C_8$-alkenyl, cyclopropyl, —$CH_2CH_2CF_3$, —$CH_2CH_2CH_2CF_3$ or cyclopropylmethyl;
$R^7$ is H or $C_1$-$C_4$-alkyl; and
$R^{8a}$ and $R^{8b}$ independently are: H, $C_1$-$C_4$-alkyl, —$NO_2$, —$NR^4R^{22}$, —$OCH_3$, —$NR^4COOR^{22}$, —Cl, —$CH_2COOR^{4a}$, —$S(O)_x$—$R^{22}$, —$NR^4CONR^4R^{22}$, —$CH_2OCO(C_1$-$C_4alkyl)$, —$NR^4COR^{22}$, —$CO_2R^{4a}$, —F, —$CH_2Ph$, or —$CONR^4R^{22}$.

5. A pharmaceutical formulation for the treatment of hypertension and congestive heart failure comprising a pharmaceutically acceptable carrier and an effective antihypertensive amount of the compound of claim 1.

6. A method of treating hypertension and congestive heart failure comprising the administration of an effective antihypertensive amount of the compound of claim 1 to a patient in need of such treatment.

* * * * *